United States Patent [19]

Borg et al.

[11] Patent Number: 5,135,956
[45] Date of Patent: Aug. 4, 1992

[54] METHOD OF USING CYTOPROTECTIVE ALCOHOLS TO TREAT NEURAL DISEASE AND NEURAL INJURY

[75] Inventors: Jacques Borg, Bischeim, France; Carl W. Cotman, Santa Ana; J. Patrick Kesslak, Irvine, both of Calif.

[73] Assignee: Regents of the University of California, Oakland, Calif.

[21] Appl. No.: 420,904

[22] Filed: Oct. 13, 1989

Related U.S. Application Data

[63] Continuation-in-part of Ser. No. 259,918, Oct. 18, 1988, abandoned, and a continuation-in-part of Ser. No. 259,919, Oct. 18, 1988, abandoned, and a continuation-in-part of Ser. No. 259,928, Oct. 18, 1988, abandoned, and a continuation-in-part of Ser. No. 259,964, Oct. 18, 1988, abandoned, and a continuation-in-part of Ser. No. 269,300, Nov. 9, 1988, abandoned.

[51] Int. Cl.$^5$ ............................................. A61K 31/045
[52] U.S. Cl. .................................... 514/724; 514/739; 514/879
[58] Field of Search ........................ 514/724, 879, 739

[56] References Cited

U.S. PATENT DOCUMENTS 4,874,794 10/1989 Katz ...................................... 514/724

OTHER PUBLICATIONS

Rothman and Olney, *Trends in Neuroscience*, 7:299-302 (1987) "Excitotoxicity and the NMDA receptor".
Lucas and Newhouse, *A.M.A. Arch. Opthalmol.*, 58:193 (1957) "The Toxic Effect of Sodium L-Glutamate on the Inner Layers of the Retina".
Olney et al., *Exp. Brain Res.*, 14:61-76(1971) "Cytotoxic Effects of Acidic and Sulpher Containing Amino Acids on the Infant Mouse Central Nervous System".
Greenamyre, *Arch. Neural.*, 43:1058-1065 (1986) "The Role of Glutamate in Neurotransmission and in Neurologic Disease".
Olney, In "Kainic Acid as a Tool in Neurobiology," (McGeer, et al., (Ed.) Raven Press, N.Y., (1978) "Neurotoxicity of Excitatory Amino Acids".
Mason and Fibiger, *Brain Research*, 155:313-329 (1978) "Kainic Acid Lesions of the Striatum: Behavioural Sequalae Similar to Huntington's Chorea".
Coyle et al., In "Kainic Acid as a Tool in Neurobiology," McGeer et al., (Ed.), Raven Press, N.Y. (1978) "Neurotriatal Injections: A Model for Huntington's Chorea".
Nadler, et al., *Nature*, 271:676-677 (1978) "Intraventricular Kainic Acid Preferentially Destroys Hippocampal Pyramidal Cells".
Olney, In "Excitatory Amino Acids in Health and Disease," Lodges (Ed.), Wiley & Sons, Ltd., England, pp. 337-352 (1988), Endogenous Excitotoxins and Neuropathological Disorders.
Simon et al., *Science*, 226:850-852 (1984), "Blockade of N-Methyl-D-Aspartate Receptors May Protect Against Ischemic Damage in the Brain".
Foster, et al., *Br. J. Pharm. Proc. Supp.*, 90:9P (1987) "Systemic Administration of MK-801 Protects Against Ischaemia-Induced Hippocampal Neurodegeneration in the Gerbil".
Wielock, *Science*, 230:681 (1985) "Hypoglycemia-induced Neuronal Damage Prevented by an N-Methyl-D-Aspartate Antagonist".

(List continued on next page.)

Primary Examiner—Glennon H. Hollrah
Assistant Examiner—Gary E. Hollinden
Attorney, Agent, or Firm—SaraLynn Mandel

[57] ABSTRACT

A method for treating or preventing neuronal injury in a mammal, comprising the step of administering in vivo a therapeutically effective amount of a long-chain fatty alcohol having from about 23 to about 29 carbon atoms or prodrug esters thereof. Also disclosed are pharmacological compositions containing from 0.01 mg/kg to about 20 mg/kg of the fatty alcohol. The method and compositions are useful in: treating traumatic injury, chemical injury and injury due to disease; promoting and accelerating recovery of behavioral function after such injury; preventing neuronal injury or death; improving training and memory functions; and protecting neurons against injury.

24 Claims, 4 Drawing Sheets

OTHER PUBLICATIONS

Ben-Ari, et al., *Brain Res.*, 165:pp. 362–365 (1979) "Evidence Suggesting Secondary Epileptogenic Lesions After Kainic Acid; Pre-Treatment with Diazepam Reduces Distant but not Local Brain Damage.

Hori, et al., *Brain Res.*, 358:380–385 (1985) "Kainic Acid Responses and Toxicity Show Pronounced $Ca^{2+}$ Dependence".

Choi, et al., *J. Neurosci.*, 7:357–368 (1987) "Ionic Dependence of Glutamate Neurotoxicity".

Kim, et al., *Neurosci.*, 23:423–432 (1987), "Quinolinate Neurotoxicity in Cortical Cell Culture".

James and Bradshaw, *Ann. Review Biochem.*, 53:259–92 (1984) "Polypeptide Growth Factors".

Edgar and Barde, *TINS*, pp. 260–262, (Jul., 1983) "Neuronal Growth Factors".

Hefti, *J. Neurosci.*, 6:2155–2162 (1986) "Nerve Growth Factor Promotes Survival of Septal Cholinergic Neurons After Fimbrial Transactions".

Williams, et al., *P.N.A.S. (USA)*, 83:9231–9235, (1986) "Continuous Infusion of Nerve Growth Factor Prevents Basal Forebrain Neuronal Death After Fimbria Formix Transection".

Perez-Polo, In Neuronal Factors, CRC Press, Boca Raton, FL (1987) "Purification of PNS Factors".

Romijn, et al., *Neurosci. Biohav. Rev.*, 8:301–334 (1984) "Towards an Improved Serum-Free, Chemically Defined Medium for Long-Term Culturing of Cerebral Cortex Tissue".

Selak, et al., *J. of Neurosci*, 5:23–28 (1985), "Pyruvate Participation in the low Molecular Weight Trophic Activity for Central Nervous System Neurons in Glia--Conditioned Media".

Thoenen and Edgar, *Science*, 229:238–242 (1985) "Neurotrophic Factors".

Borg, et al., *FEBS Letters*, 213:406–410 (1987) "Neurotrophic effect of Naturally Occurring Long-Chain Fatty Alcohols On Cultured CNS Neurons".

Gage, et al., Neuroscience 19:241–256 (1986) "Retrograde Cell Changes in Medial Septum and Diagonal Band Following Fimbria-Fornix Transection; Quantitative Temporal Analysis".

Anderson et al., *Nature*, 332:360–361 (1988), "Basic Fibroblast Growth Factor Prevents Death of Lesioned Cholinergic Neurons In Vivo".

Sunderland, *Nerves and Nerve Injuries*, Churchill Livingstone, Edinburgh (1978), pp. 69–132, "Degeneration of the Axon and Associated Changes".

Lundborg, et al., *Exp. Neurol.*, 76:361–375 (1982) "Neuron Regeneration in Silicone Chambers: Influence of Gap Length and of Distal Stump Components".

De Latorre, *Spine*, 6:315 (1981) "Spinal Cord Injury; Review of Basic and Applied Research".

Privat, *Neurosci. Lett.*, 66:61–66 (1986) "Transplantation of Dissociated Foetal Serotonin Neurons into the Transected Spinal Cord of Adult Rats".

Mishkin and Appenzeller, *Scientific American*, 256:80–89 (1987) "The Anatomy of Memory".

Myhrer, *Physiology & Behavior*, 15:433–437 (1975) "Maze Performance in Rats with Hippocampal Perforant Paths Lesions; Some Aspects of Functional Recovery".

Scheff and Cotman, *Behavioral Biol.*, 21:286 14 293 (1977) "Recovery of Spontaneous Alternation following Lesions of the Entorhinal Cortex in Adult Rats; Possible Correlation to Axon Sprouting".

Steward *Int'l Review of Neurobiol.*, 23:197–254 (1982) "Assessing the Functional Significance of Lesion-Induced Neuronal Plasticity".

Loesche and Steward, *Brain Res. Bulletin*, 2:31–39 (1977) "Behavioral Correlates of Denervation and Reinnervation of the Hippocampal Formation of the Rat: Recovery of Alternation Performance Following Unilateral Entorhinal Cortex Lesions".

Ramirez and Stein, *Behavioral Brain Res.*, 13:53–61 (1984), "Sparing and Recovery of Spatial Alternation Performance After Entorhinal Cortex Lesions in Rats".

Fass, *Behavioral and Neural Biol.*, 37:108–124 (1983) "Temporal Changes in Open-Field Activity Following Progressive Lesions of Entorhinal Cortex: Evidence for Enhanced Recovery".

Engelhardt and Steward, *Behavioral and Neural Biol.*, 29:91–104 (1980) "Entorhinal Cortical Lesions in Rats and Runway Alternation Performance: Changes in Patterns of Response Initiation".

Kimble, *Physiol. & Behavior*, 21:177–187 (1978) "Effects of Combined Entorhinal Cortex-Hippocampal Lesions on Locomotor Behavior, Spontaneous Alternation and Spatial Maze Learning in the Rat".

Ross and Grossman, *Journal of Comp. & Physiol. Psych.* 85:70–81 (1973), "Some Behavioral Effects of Entorhinal Cortex Lesions in the Albino Rat".

(List continued on next page.)

OTHER PUBLICATIONS

Steward et al., *Brain Res. Bull.*, 2:41–48 (1977), "Behavioral Correlates of Denervation and Reinnervation of the Hippocampal Formation of the Rat: Open Field Activity and Cue Utilizatain Following Bilateral Entorhinal Cortex Lesions".

Karpiak, *Exper. Neurol.*, 81:330–339 (1983) "Ganglioside Treatment Improves Recovery of Alternation Behavior After Unilateral Entorhinal Cortex Lesion".

Ramirez, et al., *Neurosci. Letters*, 75:283–287 (1987a) "Ganglioside Treatments Reduce Locomotor Hyperactivity After Bilateral Lesions of the Entorhinal Cortex".

Ramirez, et al., *Brain Res.*, 414:85–90 (1987b) "Ganglioside-Induced Enhancement of Behavioral Recovery After Bilateral Lesions of the Entorhinal Cortex".

Kaye, et al., *Biol. Psychiatry*, 17:275–279 (1982) "Modest Facilitation of Memory in Dementia with Combined Lecithin and Anticholinerestase Treatment".

Summers, et al., *Biol. Psychiatry*, 16:145–153 (1981) "Use of THA in Treatment of Alzheimer-like Dementia; Pilot Study in Twelve Patients".

Summers, et al., *New Engl. J. of Med.*, 315:1241–1245 (1986) "Oral Tetrahydroaminoacridine in Long-Term Treatment of Senile Dementia, Alzheimer-Type".

Fitten et al., *J. of Gerontology* 42:681–685 (1987) "Long-Term Oral Administration of Memory-Enhancing Doses of Tacrine in Mice: A Study of Potential Toxicity and Side Effects".

Kesslak et al., *Soc. for Neurosci. Abst.* 14:56 (1988) "Recovery on a Reinforced Alternation Task with THA Using a Sequential Lesion Model for Alheizmer's Disease".

Stein and Will, *Brain Res.*, 261:127–131 (1983), "Nerve Growth Factor Produces a Temporary Facilitation of Recovery from Entorhinal Cortex Lesions".

Bjorklund and Stenevi, *Ann. Rev. of Neurosci.*, 7:279–308 (1984), "Intracerebral Neural Implants: Neuronal Replacement and Reconstruction of Damaged Circuitries".

Cotman and Kesslak, "The Role of Trophic Factors in Behavioral Recovery and Integration of Transplants," In Progress in Brain Research, Elsevier Science Pub., in press, vol. 78 (1988).

Gash et al., *Neurobiology of Aging*, 6:131–150 (1985) "Neural Transplantation: A Review of Recent Developments and Potential Applications to the Aged Brain".

Armstrong et al., "Response of Septal Cholinergic Neurons to Axotomy", *J. Comp. Neurol.*, 264:421–436 (1987).

Barron, "Comparative Observations on the Cytologic Reactions of Central and Peripheral Nerve Cells to Axotomy" in Spinal Cord Reconstruction, Kao and Bunge, Eds., Raven Press, pp. 4–70, (1983).

Baudry, "Mechanisms of Synaptic Plasticity in Mammalian Brain: Implications for Theories of Learning and Memory in Neural Plasticity, A Lifespan Approach, Petit and Ivy, Eds., (A. R. Liss, Inc., N.Y.) pp. 125–141 (1987).

Ben-Ari, "Limbic Seizure and Brain Damage Produced by Kainic Acid: Mechanisms and Relevance to Human Temporal Lobe Epilipsy", *Neuroscinece* 14:375–403 (1985).

Bishop and Hajra, "Mechanism and Specificity of Format6ion of Long Chain Alcohols by Developing Rat Brain" *J. Biol. Chem.*, 256:9542–9550 (1981).

Buzsaki and Gage, "Neural Grafts: Possible Mechanisms of Action" in Neural Plasticity, A Lifespan Approach, Petit and Ivy, Eds., (A. R. Liss, N.Y.) pp. 171–199 (1987).

Coyle and Schwarcz, "The use of Excitatory Amino Acids as Selective Neurotoxins" *Handbook of Chem. Neuroanatomy*, vol. 1, Meth. Chem. Neuroanatomy, Bjorklund and Hokfelt, Eds., Elsvier, (1983) pp. 508–527.

Coyle et al., "Alzheimer's Disease: A Disorder of Cortical Cholinergic Innervation", *Science*, 219:1184–1190, (1983).

Gage et al., "Reinnervation of the Partially Deafferented Hippocampus by Compensatory Collateral Sprouting" *Brain Research*, 268:27–37 (1983).

Geddes et al., "Senile Plaques as Aberrant Sprout-Stimulating Structures", *Neurol.* 94:767–776 (1986).

Goldstein, "The Effects of Drugs on Mambrane Fluidity", *Ann. Rev. Pharmacol. Toxicol.*, 24:43–64 (1984).

Hagg et al., "Delayed Treatment with Nerve Growth Factor Reverses the Apparent Loss of Cholinergic Neurons After Acute Brain Damage", *Exp. Neurol.*, 101:303–312 (1988).

Kim et al., "Calcium Translocation by Fatty Acid Derivatives in a Two-Phase Partition Model", *Bioch. Biophys. Acta.*, 833:386–395 (1985).

(List continued on next page.)

OTHER PUBLICATIONS

Kromer, "Nerve Growth Factor Treatment After Brain Injury Prevents Neuronal Death", *Science*, 235:214–216 (1987).

Martin, "Huntington's Disease: New Approaches to an Old Problem", *Neurology*, 34:1059–1072 (1984).

Natarajan and Schmid, "1-Docosanol and Other Long Chain Primary Alcohols in Developing Rate Brain", *Lipid*, 12:128–130 (1977).

Natarajan et al., "Biosynthesis of Long Chain Alcohols by Developing Brain and Regenerating Sciatic Nerve", *J. Neurochem.*, 43:328–334 (1984).

Sladek et al., "Nerve-Cell Grafting in Parkinson's Disease", *J. Neurosurg.*, 68:337–351 (1988).

Smith, "Animal Models of Alzheimer's Disease: Experimental Cholinergic Denervation", *Brain Res. Reviews*, 13:103–118.

Jenq and Coggeshell, "Permeable Tubes Increase the Length of the Gap that Regenerating Axons Can Span", *Brain Research*, 408:239–242 (1987).

Williams et al., "Continuous Infusion of Nerve Growth Factor Prevents Basal Forebrain Neuronal Death After Fimbris Fornix Transection", *Proc. Natl. Acad. Sci.*, 83:9231–9235 (1986).

Mansour et al., "Transplantation of Dissociated Foetal Serotinin Neurons Transected Spinal Cord of Adult Rats", *Neurosci. Letters*, 66:61–66 (1986).

Bjorklund et al., "Mechanisms of Action of Intracerebral Neural Implants: Studies on Nigral and Striatal Grafts to the Lesioned Striatum" *TINS*, 10:509–516 (1987).

Tashiro et al., "A Calcium Activated Protease Which Preferentially Degrades the 160 Component of the Neurofilament Triplet", *Eur. J. Biochem.*, 131:41–45 (1983).

Sofroniew et al., "The Cholinergic Nuclei of the Basal Forebrain of the Rat: Normal Structure, Development and Experimentally Induced Degeneration", *Brain Research*, 411:310–331 (1987).

Nadler et al., "Preferential Vulnerability of Hippocampus to Intraventricular Kainic Acid as a Tool in Neurobiology", (McGeer et al., Eds.) pp. 219–237 (1978).

Wenk and Olton, "Recovery of Neocortical Choline Acetyltransferase Activity Following Ibotenic Acid Injection into the Nucleus Basalis of Meynert in Rats", *Brain Res.*, 293:184–186 (1984).

Wrathall et al., "Spinal Cord Contusion in the Rat: Production of Graded, Reproducible, Injury Groups" *Expr. Neurol.*, 88:108–149 (1985).

Squire, "Mechanisms of Memory", *Science*, 232:1612–1619 (1986).

Cotman and Nieto-Sampedro, "Cell Biology of Synaptic Plasticity", *Science* 225:1287–1294 (1984).

Stein et al., "Brain Damage and Recovery: Problems and Perspectives" *Behavioral and Neural Biol.*, 37:185–222 (1983).

METHOD OF USING CYTOPROTECTIVE ALCOHOLS TO TREAT NEURAL DISEASE AND NEURAL INJURY

CROSS-REFERENCE TO RELATED APPLICATIONS

This application is a continuation-in-part of copending U.S. patent applications Ser. Nos. 259,918 now abandoned; 259,919 now abandoned; 259,928 now abandoned and 259,964 now abandoned were filed on Oct. 18, 1988 and Ser. No. 269,300 filed Nov. 9, 1988 now abandoned.

FIELD OF THE INVENTION

This invention relates to methods and compositions for treating neurons, and more specifically to the use of compositions containing a long chain fatty alcohol having from about 23 to about 29 carbon atoms.

BACKGROUND OF THE INVENTION

Nerve cells, or "neurons," consist of a cell body (the "soma") and an "axon" projecting from the cell body through which nerve impulses travel. Injuries to neurons involving transection of, or damage to, the axons (termed "axotomy") characteristically result in retrograde neuronal dysfunction or death to most of these cells. Such injuries may result, for example, from trauma to the head or spinal cord, or as an unavoidable consequence of surgical procedures intended to correct certain conditions of the nervous system. In addition, damage to axons may occur as a result of neurodegenerative disease.

EXCITOTOXIC NERVE INJURY

While some types of injury include damage to axons and neuron death, as in axotomy, another type of injury to neurons is excitotoxic injury. Excitotoxic injury is believed to be a fundamental cause of neural loss in anoxic and ischemic brain damage, hypoglycemic brain damage, seizure-mediated brain damage, and possibly damage in Huntington's Disease and Neurolathyrism, as well as a complication in Alzheimer's Disease (see Rothman and Olney, *Trends in Neuroscience*, 7:299-302 (1987)).

Excitotoxic injury is produced when the concentration of an excitatory amino acid, such as glutamate, or of a compound, which is an analogue that activates excitatory amino acid receptors (an "agonist"), becomes excessive in the brain or spinal cord. The amount of excitotoxins released increases in response to abnormal conditions (i.e., seizure, hypoglycemia, etc.) and results in neural loss in the areas of concentration.

Excitotoxic injury is produced either by increased extracellular excitatory amino acids associated with pathological conditions (i.e., ischemia, epilepsy, etc.), or by the direct injection into the brain of an excitatory amino acid or specific analogue. Indeed, the pattern or progression of neural loss is very similar in excitotoxins are involved in the pathological conditions mentioned above.

Lucas and Newhouse (*A.M.A. Arch. Ophthalmol.*, 58:193 (1957)) demonstrated that peripheral administration of the amino acid glutamate causes degeneration in the inner layers of the retina. Subsequently, Olney, et al. (*Exp. Brain Res.*, 14:61-76 (1971)) showed that administration of glutamate produced damage to the brain, particularly the hypothalamic region. It was suggested that, in view of the high concentrations of L-glutamate found in the brain, the accumulation of excess glutamate might be a potential mechanism for neural loss in certain central nervous system (CNS) diseases. It was also found that the excitatory potency of a series of glutamate analogues correlated with their ability to cause neurotoxic damage leading to an excitotoxicity hypothesis of CNS damage (Id.).

Single injections of glutamate have been found to not be very potent because glutamate is removed by high-affinity uptake systems that immediately remove it from the extracellular space (Greenamyre, *Arch. Neural.*, 43:1058-1065 (1986)). Blocking uptake increases glutamate's potency (Id.). Certain known excitotoxins, such as the glutamate analogue kainate (KA), are not a substrate for uptake systems and, accordingly, produce more potent and reproducible lesions. Thus, KA has been used to produce excitotoxic lesions experimentally to study the molecular mechanism of excitotoxicity (Olney, In "Kainic Acid as a Tool in Neurobiology," (McGeer, et al., (Ed.) Raven Press, N.Y., (1978)).

It has been shown that neuronal pathology induced by various excitotoxins is quite similar to a wide spectrum of neurological insults. KA injections, for example, cause striatal degeneration of gamma-amino butyric acid neurons while sparing dopamine, glutamate, and serotonin afferents to the region. This pattern is similar to the neurochemical profile observed in Huntington's Disease (Mason and Fibiger, *Brain Research*, 155:313-329 (1978); and Coyle, et al., In "Kainic Acid as a Tool in Neurobiology," McGeer, et al., (Ed.), Raven Press, N.Y. (1978)). KA injected intra-ventricularly also creates a profile of neuronal loss in the hippocampus similar to that found in epilepsy (e.g., hippocampal fields CA3, CA4, and CA1 are extremely susceptible while the dentate gyrus and area CA2 are largely spared (Nadley, et al., *Nature*, 271:676-677 (1978)). Axon-sparing lesions produced by excitatory amino acid activators are quite similar to neuronal damage found not only in Epilepsy and Huntington's Disease but also in anoxia, ischemia, and hypoglycemia (Greenamyre, supra; and Rothman and Olney, supra). Similar observations have been made for Alzheimer's Disease and even neuronal atrophy seen in schizophrenia (see Greenamyre, suora; and Olney, In "Excitatory Amino Acids in Health and Disease," Lodges (Ed.), Wiley & Sons, Ltd., England, pp. 337-352 (1988)).

The involvement of excitatory amino acids as an underlying mechanism in pathological neurodegeneration is supported by findings that excitatory amino acid receptor antagonists such as MK-801 (Merck, Sharp & Dome, London, England), an antagonist against N-methyl-D-aspartate (NMDA), can provide protection against neuronal damage in experimental models of neuropathological conditions. Thus, administration of antagonists prevents, to varying degrees, the cell loss associated with ischemia, anoxia (*Science*, et al., 226:850-852 (1984); and Foster, et al., *Br. J. Pharm. Proc. Supp.*, 90:9P (1987)), and hypoglycemia (Wielock, *Science*, 230:681 (1985)). Excitatory amino acid antagonists also have been shown to have anti-convulsive and anti-epileptic actions. Other non-excitatory amino acid analogues, however, also have been shown to be effective in some cases. Diazepam, for example, reduces brain damage caused by intra-amygdaloid injections of KA (Ben-Ari, et al., *Brain Res*, 165: pp. 362-365 (1979)).

Excitotoxicity is also readily demonstrated in vitro, where the external environments of the neuronal tissue are more amenable to manipulation. L-glutamate and various analogues (e.g., KA and NMDA) produce substantial neurodegeneration in preparations of chick retina (Rothman and Olney, suora). Rat cortical slices have been used to demonstrate the neurotoxic action of KA (Hori, et al., *Brain Res.*, 358:380-384 (1985)). L-homocysteic acid and quinolinic acid, as well as L-glutamate and KA, are neurotoxic to mouse cortical cultures (Choi, et al., *J. Neurosci.*, 7:357-368 (1987); and Kim, et al., *Neurosci.*, 23:423-432 (1987)).

NEUROTROPHIC FACTORS

The treatment of neurons after damage has been largely through the application of polypeptide growth factors (PGF's), which are small proteins that have growth regulatory properties. These molecules have emerged as a major subset of hormones or hormone-like substances that are involved in growth regulatory processes. The criteria defining a PGF include the presence of a receptor for the PGF on the surface of the cell, the internalization of the PGF-receptor complex, and initiation of a hyperplastic or hypertrophic response (see review by James and Bradshaw, *Ann. Review Biochem.*, 53:259-92 (1984)).

Traditional neurotrophic factors are a special subclass of PGFs that have an effect on nerve cells and can be demonstrated to promote survival, growth, and differentiation of neurons (James and Bradshaw, supra). Nerve Growth Factor (NGF) and Fibroblast Growth Factor (FGF) are examples of PGFs that are also neurotrophic factors.

Traditional neurotrophic factors are known to support the survival of developing neurons and are necessary for the maintenance of differentiated neuronal properties (see review by Edgar and Barde, *TINS*, pp. 260-262, (July, 1983)). For example, NGF has been purified and shown to be necessary for the survival of developing sympathetic neurons, and to reduce the incidence of death in certain neurons when administered into the brain prior to or simultaneously with the occurrence of axotomy (Hefti, *J. Neurosci.*, 6:2155-2162 (1986); and Williams, et al., *P.N.A.S. (U.S.A.)*, 83:9231-9235 (1986)). NGF appears to exert its effect only on cholinergic neurons (i.e., those cells which release the neurotransmitter acetylcholine (ACh)).

Smaller molecules (e.g., substrates for metabolism, lipid precursors, and enzyme cofactors) may act similarly to neurotrophic factors but do not fall into the same, class as the term "neurotrophic factor" is currently used in practice; that is, molecules serving metabolic functions are not neurotrophic factors in the traditional sense. There is a new category of compounds that exhibit many of the properties of traditional neurotrophic factors. These compounds are the subject of the present invention. They are "trophic" in the sense that they promote neuron growth and survival; however, they differ from traditional neurotrophic factors as they are not presently implicated in neuron differentiation, and are not peptides. Nevertheless, because of their trophic properties, they are referred to herein as "neurotrophic" compounds.

The study of neurotrophic factors has employed in vitro (cell culture) and in vivo systems to explore both morphological and physiological roles of these substances.

Cell culture experiments on neuronal cells may define requirements in vitro but do not always predict in vivo results. Several non-neurotrophic factors will improve neuronal growth, survival and differentiation in vitro, but may have little or no effect on neurons in vivo. This is particularly true when defined media are used.

Even subtle changes in media may alter neuronal survival, growth and differentiation, and have been the subject of numerous studies (Perez-Polo, In Neuronal Factors, CRC Press, Boca Raton, Fla. (1987)). Romijn, et al. (*Neurosci. Biohav. Rev.*, 8:301-334 (1984)), for example, have studied extensively different growth requirements and suggested the inclusion of various lipids and other molecules in the cell culture medium. The media of Romijn, et al. (suora), included linoleic acid, lipoic acid, and retinoic acid. Some additions affect neuronal survival; others neurite outgrowth, branching, and/or differentiation. As another example, pyruvate has been reported to have survival-promoting capacity for neurons (Selak, et al., *J. of Neurosci.*, 5:23-28 (1985)). Pyruvate is a small molecule that is a simple intermediary metabolite. In previous media pyruvate was present, but the amounts were too low relative to other ingredients to support cell survival. Finally, certain proteins can enhance neuronal survival and growth in vitro (e.g., laminin) but are present in sufficient amounts in vivo. Improvements in neuron growth, survival and differentiation in vitro after addition of a substance may thus result from enrichment of a medium which may be lacking in a particular nutrient. These studies illustrate that experiments on neurons in vitro do not necessarily predict in vivo outcome.

Moveover, a substance may demonstrate no in vitro effect yet exhibit in vivo action on target cells. For example, NGF has little if any effect on the survival or neurite outgrowth of cultured brain neurons yet has been demonstrated to enhance the survival of damaged cholinergic neurons in vivo (Hefti, supra, and Williams, et al., supra). Cell culture experiments, therefore, would not have predicted the in vivo effects of NGF.

As is well understood, such limited in vitro results are insufficient to infer, with any degree of confidence or predictability, the in vivo activity and utility of such compounds. The reported in vitro studies do not duplicate exactly the complete in vivo environment in which a mature central or peripheral nervous system functions. A multitude of unknowns remain after such work, including the ability of the compound to cross the blood-brain barrier; the effect of the compound on mature (as opposed to fetal) cells; and the effect in vivo of other associated cells, both glial cells and adjacent neurons, on neuronal survival, extension of neurites, and recovery of function. Moreover, such studies do not provide meaningful guidance on the availability in vivo of the active ingredient; localization of the compound in vivo; interference of other physiological compounds or materials on the efficacy of the compound; effect on noncortical neurons, including gabaergic and glutaminergic cells; and metabolism of the compound in vivo. Nor does such in vitro work provide information regarding the effect of the compound on cells that have suffered chemical injury, and the reported work is not suggestive of any protective effect or therapeutic properties in treatment of trauma or disease.

Verification of a physiological role for substances tested in vitro is, therefore, necessary. Verification of putative growth factors, for example, may consist of purification of the substances and the production of specific antibodies capable of neutralizing the substances in vivo (Thoenen and Edgar, *Science,* 229:238–242 (1985)), or may be made by assessment of neuronal survival after axotomy and treatment with the substances in animals (Hefti, supra and Williams, et al., supra).

Borg, et al. (*FEBS Letters,* 23:406–410 (1987)), demonstrated that the long-chain fatty alcohol n-hexacosanol (26 carbons) caused an increase in the outgrowth of processes extending from the nerve cell body and an increase in two neuron-specific enzymes: phosphate-activated glutaminase and neuron-specific enolase, after 24 hours in vitro. These effects persisted for 48 hours. The culture medium used was a defined media (Eagle Dulbecco medium supplemented with insulin, transferrin, progesterone, estradiol, selenium, putrescine, and potassium chloride) suitable for short-term culture of brain neurons. The results were consistent with an increase in the rate of growth and maturation of the cultured cortical neurons; however, no data on in vitro or in vivo cell survival were reported.

There are several types of neurons in the mammalian brain. Cholinergic neurons are found within the mammalian brain and project from the medial septum and vertical limb of the diagonal band of Broca to the hippocampal formation in the basal forebrain. The short, nerve-like portion of the brain connecting the medial septum and vertical limb of the diagonal band with the hippocampal formation is termed the "fimbria-fornix." The fimbria-fornix contains the axons of the neurons located in the medial septum and diagonal band (FIG. 1). An accepted model of neuron survival in vivo is the survival of septal cholinergic neurons after fimbriafornix transection, also termed "axotomy." Axotomy severs the cholinergic neurons in the septum and diagonal band that project to the hippocampal formation and results in the death of up to one-half of the cholinergic neurons (Gage, et al., *Neuroscience* 19:241–256 (1986)).

Studies have shown that chronic intra-ventricular administration of NGF before axotomy will prevent cholinergic neuron death in the septum (Hefti, supra, and Williams, et al., supra), and that FGF administered before or even after axotomy reduces the death of cholinergic neurons in the medial septum and the diagonal band of Broca after axotomy in young adult, and aged rats (Anderson, et al., *Nature,* 332:360–361 (1988).

Fimbria-fornix transection thus provides a suitable in vivo model for determining at various points in time the ability of various substances suspected of having an action on neurons to prevent retrograde neuronal death.

PERIPHERAL NERVES

Damage to a peripheral nerve fiber can involve either the temporary interruption of conduction without loss of axonal continuity, or the actual loss of axonal continuity resulting in the degeneration of the neuron, known as "Wallerian degeneration." In this latter case, the restoration of the continuity between the end organ and its corresponding neuron depends on regeneration of the intact portion of the axon. In order to ensure that the regenerating axon is directed back to the end organ which it originally innervated, it is necessary that the general arrangement of the endoneurium be preserved. Severance or disorganization of the entire nerve fiber may result in the absence of regeneration or the failure to innervate the correct organ. The probability of a successful regeneration will significantly decrease in the case of an extensive gap in injured nerves.

If regeneration has occurred and appropriate end organ relationships have been restored, the functional recovery involves additional processes (e.g., maturation of the newly reinnervated endoneurial tube and the recovery of sufficient number of fibers to give a response to voluntary effort or to a sensory stimulus (S. Sunderland, in *Nerves and Nerve Injuries,* Churchill Livingstone, Edinburgh (1978), pp. 69–132)).

The surgical treatment of the injured nerve will tend to restore the nerve trunk continuity, using microsurgical techniques. However, the results of peripheral nerve surgery are unpredictable, even when the most favorable conditions have been obtained. The distance of the Wallerian degeneration, the nature of the tissue intervening between the sutured nerve ends, and the condition of the nerve bed are some factors that may influence the course of regeneration and the quality of the recovery after surgery.

When somatic nerves are transected, the distal part of the severed axons die and the proximal part regenerates. In order to get the regenerating axons as close as possible to previously-innervated structures, the regenerating axons may be guided towards the distal stump by placing the stumps of the transected nerve in an impermeable tube (G. Lundborg, et al., *Exp. Neurol.,* 76:361–375 (1982)).

The maximal length that regenerating axons can cross is ordinarily approximately 10 mm.

One compound that has been demonstrated to have neurotrophic properties in vitro is 1-n-hexacosanol, a straight chain saturated fatty alcohol having 26 carbon atoms (Borg, et al., *FEBS Letters,* supra). In monolayer cultures of fetal rat brain cells, it was demonstrated to facilitate neurite extension and to increase the total protein, as well as the glutaminase and enolase activity of the treated cultures, in comparison to controls.

Spinal Cord Injuries

Traumatic injuries to the mammalian spinal cord result in severe motor and sensory deficits, eventually in total and permanent paraplegia. However, concussive, contusive, or compressive lesions often result in an initial sparing of function which may be followed by additional functional recovery. The degree of initial deficit and subsequent recovery are undoubtedly related to the physiological severity, the degree of ischemia, and the anatomical extent of the lesion. The fact that sparing and recovery can occur has encouraged attempts to develop improved methods for treating spinal cord injury. Such treatment would focus on either limiting the damage produced acutely by the initial injury, or promoting the regeneration of axons during the later stages after injury (De Latorre, *Spine,* 6:315 (1981)). The histopathological changes at the site of injury are described as progressive ischemic necrosis; they are initiated by an inadequate vascular perfusion of the injured tissue that results in cell death, cystic degeneration, and cavitation. This necrotizing process may continue for weeks and even months; as a result, the initial narrow, well-circumscribed lesion may become as long as several vertebral segments. During this time, fibroblasts and astrocytes will proliferate and invade the spinal cord and surrounding tissue, forming a fibrous meshwork that segregates the necrotic region from the normal tissue; this environment would certainly impair the possibility of axonal growth into the lesion. Thus, even if CNS axons were to possess sufficient intrinsic growth capacity for effective regeneration, there are many reasons why this capacity would be inhibited from full expression.

Pharmacological experiments have been conducted with the aim of improving conditions at the site of injury so as to minimize acute neuronal damage and thereby reduce functional loss and promote neuroregeneration. Most of these treatments have been designed to reduce the damaging effects of tissue ischemia; and recent studies with steroid hormones, naloxone, and thyrotropin-releasing hormone seem very promising. If the severity of the necrotizing histopathological reaction can be reduced in this way, it should be possible to design treatment protocols in which spinal injuries are treated initially with drugs designed to reduce edema and ischemia and, subsequently, with agents designed to promote axonal growth.

On the other hand, transplantation of nervous tissue to the spinal cord has been attempted on animals and has been shown to improve the regeneration after an injury. Several models have been used, including intraspinal bridges, transplants of glial cells, bridges of peripheral nerves, or replacement of missing supra-spinal afferents (Privat, *Neurosci. Lett.*, 66:61-66 (1986)). However, the functional recovery after such transplantation is often deceptive and improvement of this method is needed before it can be attempted on patients.

FACILITATION OF LEARNING AND MEMORY

Successful outcomes from treatment of injured neurons includes recovery of behavioral functions of the neurons. Recent research in animals having complex nervous systems, including humans and primates, has shown that there are several distinct types of behavior. A critical type is learning, memory, and higher cognition functions of behavior relevant to injury, neurodegenerative diseases, and the recovery of function. Damage to specific brain areas from trauma or disease can preferentially compromise learning or memory functions, including higher cognitive functions.

Learning and memory can be broadly defined as "changes in behavior resulting from prior experience." Most research has been concerned with basic mechanisms for learning, defining the learning systems, and discovering beneficial interventions; for example, those that promote behavioral recovery after injury. The hippocampus and entorhinal cortex of the limbic system are believed to play a critical role for processing information in learning and memory (Mishkin and Appenzeller, *Scientific American*, 256:80-89 (1987)). These structures and their associated memory functions are extremely vulnerable to injury from a variety of diseases; in particular, epilepsy, stroke and Alzheimer's Disease.

Damage to the entorhinal cortex results in learning and memory impairments for a variety of tasks (Myhrer, *Physiology & Behavior*, 15:433-437 (1975); Scheff and Cotman, *Behavioral Biol.*, 21:286-293 (1977); and Stewart, *Int'l. Review of Neurobiol.*, 23:197-254 (1982)). Impairments after entorhinal damage vary according to the extent of the loss of neural input to the hippocampal region and the type of behavioral task confronting the subject. After unilateral entorhinal lesions, spatial alternation deficits have been reported for the T-maze test (Loesche and Steward, *Brain Res. Bulletin*, 2:31-39 (1977); and Scheff and Cotman, supra: Y-maze (Ramirez and Stein, *Behavioral Brain Res.*, 13:53-61 (1984)); and the Hebb-Williams maze (Myhrer, supra)). Unilateral and bilateral entorhinal lesions also produce a transient hyperactivity reaching a peak 4-6 days post-lesion (Fass, *Behavioral and Neural Biol.*, 37:108-124 (1983)). More persistent deficits occur in tasks involving spatial memory after bilateral entorhinal cortex damage (Engelhardt and Steward, *Behavioral and Neural Biol.*, 29:91-104 (1980); Kimble, *Physiol. & Behavior*, 21:177-187 (1978); Loesche and Steward, supra, Ramirez and Stein, supra; Ross and Grossman, *Journal of Comparative & Physiol. Psych.* 85:70-81 (1973); Steward et al., Brain Res. Bulletin, 2:41-48 (1977)). However, behavioral recovery in spatial tasks can be observed with extensive training after bilateral entorhinal damage (Ramirez and Stein, supra). It thus appears that the integrity of the entorhinal-hippocampal circuit is not essential for learning tasks involving spatial memory, though damage to this system greatly impairs the rate of learning.

Studies on restoring learning and memory function after brain damage illustrate the complexities of understanding behavioral recovery. Interventions thus far have included conventional pharmaceutical agents, gangliosides, nerve growth factors, and brain transplants. For example, the rate of recovery from learning deficits after entorhinal lesions can be accelerated by various treatments. Administration of gangliosides (sialic acid-containing glycosphingolipids located in the neuronal cell surfaces) increased the rate of recovery from hyperactivity and in spatial memory tasks (Karpiak, *Exper. Neurol.*, 81:330-339 (1983); Ramirez, et al., *Neurosci. Letters*, 75:283-287 (1987a); and Ramirez, et al., *Brain Res.*, 414:85-95 (1987b)). The mechanisms by which gangliosides ameliorate injury are largely unknown.

Other conventional (or non-conventional) drugs which act on the cholinergic system (the group of neurons which release the neurotransmitter acetylcholine) may also influence recovery. Recent studies suggest that behavioral function can be enhanced by administration of the anti-cholinesterase tetrahydroaminoacridine (THA), which provides larger neurotransmitter pools and potentiates the system. Preliminary clinical reports have noted behavioral improvement after administration of THA to patients with Alzheimer's Disease (Kaye, et al., *Biol. Psychiatry*, 17:275-279 (1982); Summers, et al., *Biol. Psychiatry*, 16:145-153 (1981); and Summers, et al., *New. Engl. J. Of Med.*, 315:1241-1245 (1986)). Animal studies have also demonstrated that chronic administration of THA can improve memory in normal and impaired, aged mice (Fitten, et al., *J. of Gerontology*, 42:681-685 (1987)); and in rats with unilateral lesions of the entorhinal cortex (Kesslak, et al., *Soc. for Neurosci. Abstr.*, 14:56 (1988)). Nerve growth factor (NGF) has been shown to increase the rate of recovery in spatial alternation tasks after entorhinal lesions, possibly by acting on cholinergic pathways (Stein and Will, *Brain Res.*, 261:127-131 (1983)).

NEURAL IMPLANTS

Pharmacological interventions are not the only means for promoting behavioral recovery after CNS damage. Replacement of specific neurons or neurotransmitters is possible using partial brain transplants (e.g., consisting of fetal neurons or glial cells). In the last ten years, there has been a dramatic increase in the use of partial brain transplants in animal models for neurodegeneration due to aging, disease, and trauma. Transplants have been quite successful in mediating behavioral recovery in a variety of tasks (for reviews, see: Bjorklund and Stenevi, *Annual Review of Neurosci.*, 7:279-308 (1984); Cotman and Kesslak, "The Role of Trophic Factors in Behavioral Recovery and Integration of Transplants," In Progress in Brain Research, *Elsevier Science Pub.*, in press, Vol. 78 (1988); and Gash, et al., *Neurobiology of Aging*, 6:131-150 (1985)). While it might be assumed that transplants promote behavioral recovery by restoring damaged circuitry, this is not necessarily the case. Transplants may act on several levels to stimulate behavioral recovery. For example, transplants might not only reconnect interrupted circuitry, they might also make available more neurotransmitters to facilitate the operation of existing circuits. Transplants might also stimulate vascularization, remove toxic substances, or promote neuronal survival and growth via neurotropic interactions between host and transplant.

There exists a need for methods of treatment of injured neurons in vivo using compositions which can promote the survival of neurons, protect the neurons against excitotoxicity, and promote recovery of behavioral function. The present invention satisfies this need and provides related advantages as well.

SUMMARY OF THE INVENTION

The present invention is grounded in the surprising discovery that hexacosanol and analogues and homologs thereof, including saturated and unsaturated straight chain alcohols of preferably from about 23 to about 29 carbon atoms, or prodrug esters thereof, exhibit powerful neurotrophic and neuroprotective effects in vivo on neurons. Not only does this material facilitate extension of neurites in vivo, it also facilitates healing of traumatic injury to both the central and peripheral nervous systems, by increasing extension of neural processes, facilitating reconnection and reestablishment of function, decreasing ischemia and neuronal death, and reducing Wallerian degeneration after injury. Moreover, the compounds of the present invention are useful in the treatment or prevention of neural degeneration, including neurodegenerative diseases and neuron loss or damage related to chemical or environmental factors and injury from excitatory amino acids, such as glutamic acid and other endogenous materials.

Moreover, the compounds of the present invention, unlike previously described neurotrophic materials, can cross the blood-brain barrier, making them much more useful in the treatment of neurons of the central nervous system.

Thus, the present invention provides a method for treating or preventing neuronal injury in vivo, comprising the step of administering to a mammal a pharmaceutically effective amount of a long-chain fatty alcohol having from about 23 to about 29 carbon atoms, or prodrug esters thereof.

Thus, the present invention provides a method for treating injured neurons in a mammal, comprising the step of administering in vivo a therapeutically effective amount of a long-chain fatty alcohol having from about 23 to about 29 carbon atoms, or prodrug esters thereof. The injury treated can be traumatic injury, chemical injury, or injury due to disease or congenital condition. Diseases in which the present invention is believed to be applicable include Alzheimer's Disease, Huntington's Chorea, other neurodegenerative diseases, such as Epilepsy and Parkinson's Disease, developmental diseases of the CNS such as Cerebral Palsy, some aging processes of the brain, and perhaps even genetic disorders such as Down's Syndrome. In a preferred embodiment, the amount of composition administered is effective to increase the number of surviving neurons after the treatment, or to increase the outgrowth of processes from injured neurons. Furthermore, the method may include the step of grafting neurons into the site of the injury, including fetal tissue, placental tissue or genetically modified cells. Preferably, the amount of administered compound is sufficient to reduce Wallerian degeneration.

The present method has particular applicability in treating or preventing brain injury related to neurosurgery, and the administering step is performed in conjunction with the surgery.

In accordance with another aspect of the present invention, the long-chain fatty alcohol is obtained from an extract of a plant in which the alcohol is naturally present.

In accordance with another aspect of the present invention, there is provided a method for facilitating neuronal function in a mammal, comprising the step of administering in vivo an effective neuroprotective amount of a long-chain fatty alcohol having from about 23 to about 29 carbon atoms, or prodrug esters thereof. The alcohol is preferably hexacosanol. In one embodiment, the fatty alcohol protects the neurons from damage or death due to exposure to neurotoxic agents, such as heavy metals or neuroexcitatory compounds, of which glutamate and glutamate analogs are examples. The method may further comprise the co-administration of an effective amount of a second neurotrophic or neuroprotective compound, or a second long-chain fatty alcohol having from about 23 to about 29 carbon atoms, or prodrug esters thereof. These neurotrophic or neuroprotective compounds may be selected from the group consisting of nerve growth factor, fibroblast growth factor, somatomedins, benzodiazepines, kappa receptor agonists, calcium channel blockers and excitatory amino acid receptor antagonists.

In accordance with a further aspect of the present invention, there is provided a pharmaceutical composition, comprising an aqueous, physiologically acceptable injectable carrier and an effective neurotrophic or neuroprotective amount of a long-chain fatty alcohol having from about 23 to about 29 carbon atoms, or prodrug esters thereof. The composition may advantageously further comprise an effective amount of a solubilizer for the alcohol, such as a protein or a surface active agent. Moreover, the composition can additionally comprise a second active ingredient, which may be a neurotrophic or neuroprotective compound. Compositions including a second long-chain fatty alcohol are also contemplated.

In accordance with still another aspect of the present invention, there is provided a pharmaceutical composition, comprising an effective neurotrophic or neuroprotective amount of a long-chain fatty alcohol having from about 23 to about 29 carbon atoms, or prodrug esters thereof; sufficient solubilizer to render the alcohol soluble in aqueous media; and a water-miscible pharmaceutically acceptable excipient.

Another embodiment of the invention provides a pharmaceutical composition in dosage unit form, comprising an effective neurotrophic or neuroprotective amount of a long-chain fatty alcohol having from about 23 to about 29 carbon atoms or prodrug esters thereof; and a pharmaceutically acceptable excipient The alcohol may be synthetically produced or may be in the form of an extract from a plant in which the alcohol naturally occurs. In a preferred embodiment, the amount of the fatty alcohol in the dosage unit is between about 0.5 mg and about 500 mg. The excipient may be in the form of an injectable carrier, an oral vehicle, or any other suitable form.

In accordance with another aspect of the present invention there is provided a method of protecting neurons against loss of function in vivo, by administering a therapeutically effective amount of compositions containing one or more long-chain fatty alcohols having from about 23 to about 29 carbons, or prodrug esters thereof, and preferably hexacosanol. The compositions may also include compounds that are antagonists of excitotoxic amino acids or antagonists against agonists of excitotoxic amino acids.

Treatment of neurons using the methods of the invention may include transplantation of biological materials or synthetic biocompatible materials to promote reconnection and restoration of function of the surviving neurons.

Treatment may be administered prior to, concurrent with, or following excitotoxic injury. The compositions may also include compounds that are antagonists of excitatory amino acids.

Treatment of neurons using the methods of the invention may include transplantation of biological materials or synthetic biocompatible materials to promote reconnection and restoration of function of the surviving neurons.

In accordance with a further aspect of the present invention is a method for improving training and memory functions in patients that have sustained damage to neurons of the brain comprising administering in vivo, a therapeutically effective amount of a composition containing one or more long-chain fatty alcohol having from about 23 to about 29 carbons, or prodrug esters thereof. Furthermore, the composition may be administered by means of injection intra-cerebrally, intra-peritoneally, intra-muscularly, intra-ventricularly, intravenously, collatopically, orally, sublingually, bucally, vaginally, parenterally or via implantation or infusion methods.

The present invention also includes a method for reducing the rate of impairment to behavioral function to neurons in vivo, comprising administering to neurons that have sustained or will sustain trauma or disease, in vivo, a therapeutically effective amount of a composition containing one or more long-chain fatty alcohol and a compound that promotes behavioral recovery.

A further aspect of the present invention is the use of a composition comprising one or more long-chain fatty alcohols having from about 23 to about 29 carbons, or prodrug esters thereof, in the preparation of a medicament for use in practicing the methods set forth above which comprises mixing a pharmaceutically effective amount of the fatty alcohol with a physiologically acceptable carrier.

DETAILED DESCRIPTION OF THE INVENTION

In order that the invention herein described may be more fully understood, the following detailed description is set forth.

The invention provides methods for promoting the survival of neurons having sustained injury likely to result in dysfunction or death in vivo by administering compositions containing long-chain fatty alcohols, such as hexacosanol or analogues of hexacosanol. The injury may result from trauma to the neurons as a result of surgery or accident, or as a result of neurodegenerative disease.

According to a preferred embodiment of the invention, the 26 carbon fatty alcohol n-hexacosanol as described by Borg, et al. (*FEBS Letters*, 23:406–410 (1987)), incorporated by reference herein, and commercially available (Fluka A-G, Bern, Switzerland or SIGMA Chemical Company, St. Louis, Mo.), is provided in a suitable, pharmaceutically-acceptable carrier to treat injured neurons in vivo. Other long-chain fatty alcohols that may be used in the method of the invention include long-chain fatty alcohols having from 23 to 29 carbons, or prodrug esters thereof.

These long-chain fatty alcohols, their use contemplated in the present invention, may be synthesized, obtained commercially or extracted in a plant extract form from plants which product these long-chain fatty alcohols and contain these alcohols. Such extracts may be produced by extracting the plant extract with an organic solvent and subsequently removing it to produce a purified extract. Specifically, the tropical plant *Hygrophila erecta* Hochr. contains such long-chain fatty alcohols, which may be extracted from the plant with a variety of organic solvents, specifically a chloroform/methanol mixture. Such plant extracts may include additional components which separately or in conjunction with the associated long-chain fatty alcohols may produce the desired effects as contemplated by the present invention.

The neurons to be treated by the method of the invention are preferably CNS cholinergic neurons, but non-cholinergic neurons may be susceptible to such treatment as well. Moreover, such treatment may be effective for ameliorating damage to the peripheral nervous system (PNS) as well.

Figure 1A:
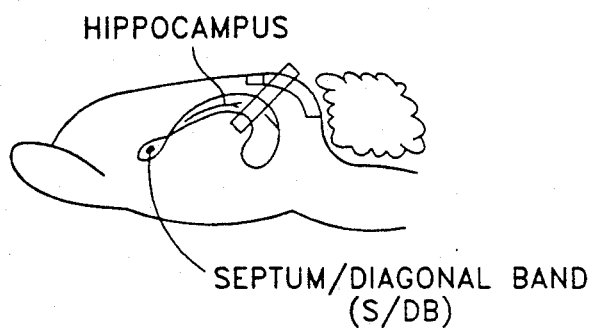
FIGS. 1A and 1B depict the regions of the brian, including the fimbria-fornix.
Figure 1B:
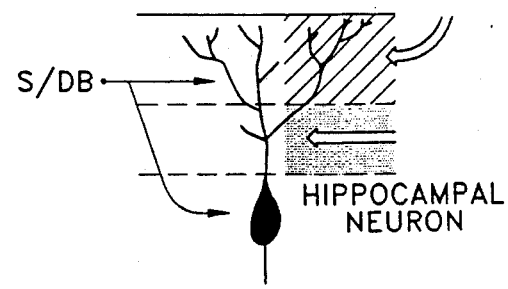

The method of the invention is exemplified by a first embodiment in which n-hexacosanol is injected intraperitoneally (i.p.) into an animal model prior to surgical axotomy. The enzyme acetylcholinesterase (AChE) is localized to cholinergic neurons and is, therefore, a marker for brain cholinergic neurons in histological preparations. AChE is used to detect cholinergic neurons in the septal region of the brain (FIG. 1) after axotomy, by counting the number of large AChE-positive neurons ipsilateral to the transection and comparing to control neurons on the undamaged contralateral side (Anderson, et al., *Nature (Letters*, 332:360-361 (1988)). Cresyl violet, which stains Nissl bodies and thus all living cells, is used to verify the data obtained from AChE staining.

Treatment with the hexacosanol resulted in enhanced survival of cholinergic neurons in the medial septum (MS) and vertical diagonal band (VDB) of the forebrain. Without being bound by any theory, it is believed that certain long-chain fatty alcohols, such as hexacosanol and its analogues, may promote neuron survival by facilitation of endogenous neurotrophic factors that then act on the injured neurons. The hexacosanol appears to function to protect neurons from dysfunction and death as a result of trauma or disease, as well as to rescue injured neurons from cell death.

Unexpectedly, we have found that long-chain fatty alcohols such as hexacosanol, when administered in vivo, protect neurons from excitotoxic injury. Accordingly, the present invention provides methods for treating the neurons with compositions containing long-chain fatty alcohols having from 23 to 29 carbons, or prodrug esters thereof, such as hexacosanol or analogues of hexacosanol. The invention includes methods of enhancing the action of known excitotoxic amino acid antagonists using hexacosanol in combination with the antagonists.

Hexacosanol may act by inhibiting the binding of excitatory amino acids to their receptors or by changing membrane properties of the neurons; it has been shown that long-chain fatty acids and their related alcohols may either increase or decrease membrane fluidity, which would then modify the membrane excitability of CNS neurons (D. B. Goldstein, *Ann. Rev. Pharmacol. Toxicol.*, 24:43-64 (1984)). Hexacosanol may also change the calcium fluxes that are involved in neuronal death related to ischemic conditions (Meldrum, *Adv. Neurol.* 44:849-855 (1986)). Intracellular calcium and the calcium-dependent protease (calpain) have been shown to play an important role during the development period and in a variety of degenerative phenomena (Y. Tashiro, et al., *Eur. J. Biochem.* 131:41-45 (1983)). Thus, a high level of intracellular calcium may result in the degeneration of axonal branches (M. Baudry, in: *Neural Plasticity: A Lifespan Approach*, A. R. Liss (1988) pp. 125-141). Long-chain alcohols have been shown to alter calcium influx through excitable membranes (preliminary results: R.S. Kim and F.S. La Bella, *Bioch. Biophys. Acta* 833:386-395 (1985)). Thus, hexacosanol may be used by neurons to buffer intracellular calcium levels in mitochondria, therefore preventing the activation of calcium-dependent processes such as calpains. These neuronal populations would survive, while others lacking this buffer system will be at greater risk to be eliminated.

We believe that long-chain alcohols may participate in the control of brain plasticity during development and in adult CNS. These compounds may be used to increase the survival of neuronal populations during developmental periods that require the establishment of appropriate neuronal connections. Long-chain alcohols have also been shown to be synthesized and metabolized by rat brain during development (J. E. Bishop and A. K. Hayra, *J. Biol. Chem.* 256:9542-9550 (1981); V. Natarajan, et al., *J. Neurochem.* 43:328-334 (1984)). This is the case during the neonatal period, as well as during the process of learning and memory in the adult. Short-term memory may involve regulation of calcium, while long-term memory may entail more enduring structural changes such as growth of additional synaptic contacts or enlargement of existing contacts.

The method of the invention is also exemplified by a second embodiment in which n-hexacosanol is injected peripherally (intra-peritoneally) and intra-cerebrally into an animal model, both prior to intra-cerebral injection of the excitotoxin KA and following injections of KA. Treatment with the hexacosanol resulted in protection against excitotoxic lesions as evidenced by decreased neural loss when compared with untreated controls.

The method of the invention is also exemplified by a third embodiment in which n-hexacosanol is infused into an animal model prior to lesion of the entorhinal cortex region of the brain. The rate of behavioral recovery after entorhinal lesions was increased as a result of treatment with hexacosanol as compared to untreated, lesioned animals.

Because long-chain fatty alcohols such as hexacosanol and analogues of hexacosanol promote neuron survival in vivo, such molecules are useful for therapy in neurodegenerative disorders where functional axotomy occurs in the course of the disease; and for the treatment of neural trauma resulting from spinal cord or head injuries. Such molecules can be used alone, in combination, or could be combined with neurotrophic factors such as NGF and FGF or substances having neurotrophic-like activity.

Moreover, because known antagonists of excitatory amino acids have been shown to provide protection against neuronal damage from excitotoxicity, the methods of the invention also contemplate the use of hexacosanol in combination with antagonists of excitatory amino acids, such as MK-801 (Merck, Sharp and Dome, London, England) an antagonist of NMDA; or antagonists against receptors such as kainate receptors, quisqualate receptors or N-methyl-D-aspartate receptors to enhance the effect of such antagonists; or the use of hexacosanol in combination with antagonists of excitatory amino acid agonists, to reduce excitotoxic damage to neurons.

The methods of the invention also contemplate use of hexacosanol in combination with other compounds that appear to exhibit beneficial effects on the recovery of behavior after neural injury These compounds include gangliosides and nerve growth factor. On the other hand, transplantation of nervous tissue to the spinal cord has been attempted on animals and has been shown to improve the regeneration after an injury. Several models have been used, including intraspinal bridges, transplants of glial cells, bridges of peripheral nerves, or replacement of missing supra-spinal afferents (Privat, *Neurosci. Lett.* 66:61-66 (1986)). Furthermore, accelerated behavioral recovery of neurons may be achieved by combining hexacosanol with transplantation, for example, using cells such as fetal neurons or glial cells.

The compositions of the methods of the invention containing hexacosanol and analogues of hexacosanol may be administered in vivo using conventional modes of administration which include, but are not limited to, intra-peritoneal, intra-venous, intra-cerebral, intra-muscular, or intra-ventricular injection; or they may be administered orally. Alternatively, the compositions may be introduced into the region of injured neurons by means of implanted polymers impregnated with the compositions; for example, Elvax ® (Dupont, Wilmington, Del.) for release of the compositions over time. The compositions may include conventional pharmaceutically-acceptable carriers known in the art, such as alcohols (e.g., ethyl alcohols), serum proteins, human serum albumin, liposomes, and buffers (including phosphates), water, sterile saline or other salts, or electrolytes.

Administration of the compositions to humans, in the methods of the invention, should, of course, be performed after standard toxicity studies to determine any toxic effects and safe dosages for treatment.

The most effective mode of administration and dosage regimen for the compositions used in the methods of this invention will depend upon the severity and course of the injury or disease, the patient's health and response to treatment, and the judgment of the treating health professional. Accordingly, the dosages of the compositions should be titrated to the individual subject. Nevertheless, an effective dose may be in the range from about 0.01 mg/kg to about 100 mg/kg body weight; preferably from about 0.5 mg/kg to about 10 mg/kg; and, most preferably, from about 0.5 mg/kg to about 5 mg/kg.

The compositions of the invention, for example, containing n-hexacosanol, are administered to neurons of the CNS and/or PNS by introducing the compositions prior to, concurrently with, or following the incidence of trauma or onset of disease. Thus, the hexacosanol or analogues may be introduced in vivo preceding injury; for example, before surgery, for the purpose of obtaining a protective effect against neuron death. The administration of treatment may also be performed at regular pre-set intervals preceding the injury. Appropriate timing of the administration of the hexacosanol may be determined clinically in patients by a skilled professional or in animal models. For preventative treatment, a patient suspected of propensity for the disease may be tested, for example, by genetic testing methodology; and appropriate dosages of hexacosanol may then be administered.

The compositions of the present invention may be administered in vivo using a variety of conventional modes of introduction to the neuronal tissue in individual dosages, including injections intravenously, intramuscularly, intracerebrally, or intraperitoneally. Additionally, the hexacosanol may be administered topically, orally, sublingually, bucally, vaginally, parenterally, or via implantation or infusion methods.

Parenteral compositions may be provided containing the active composition and any of the well-known injectable carriers. The term "parenteral" as used herein includes subcutaneous injection, intravenous, intramuscular, or intrasternal injection; or infusion techniques. The parenteral composition not only includes the active ingredient but will also preferably include a physiologically-acceptable surface active agent, either ionic or non-ionic, as well as conventional preservatives. Injectable carriers can be solvent or dispersion media containing, for example, water, ethanol, glycerol, hydroxymethylcellulose, propylene glycol, polyethylene glycol, polyoxyethylenesorbitan, and vegetable oils. The injectable solutions may include conventional antibacterial or antifungal agents, such as parabens, chlorobutanol, phenol, sorbic acid, thimerosal, and the like.

In addition, buffers may be used to maintain the composition at physiological pH or at a slightly lower pH (e.g., 5 or 6). The solutions may be made isotonic by the addition of conventional materials, such as sodium chloride and/or sugars. Surface active agents may be selected from the conventional categories of those materials, including polyoxyethylenes or polyoxyalkylenes, sorbitan derivatives, and the like. Other solubilizing agents include proteinaceous solubilizers, such as albumin, and water-miscible alcohols, such as ethanol.

In a preferred embodiment, the long-chain fatty alcohols are formulated into oral or injectable compositions, and may be provided in individual dosage units. Each unit may contain a pharmacologically-effective amount of active ingredient. For instance, the following example contemplates the use of a long-chain fatty alcohol for use in the manufacture of solutions for injection. For example, 9 mg of sodium chloride may be dissolved with stirring in 800 ml of water suitable for injection purposes and pH-adjusted to between 5 and 7 (preferably 6.5) with phosphate buffer. To produce a final injectable long-chain fatty alcohol individual dosage unit comprising 100 mg per ml, there is dissolved or dispersed with stirring 100 g of the specific fatty alcohol, in combination with a solubilizing surfactant. The pH is controlled and, if necessary, it is again adjusted with buffer. Finally, the volume is brought up to 1 liter with water suitable for injection purposes, and the pH is again checked.

The carrier may comprise pharmaceutically-acceptable carriers known in the art, such as alcohols, albumin proteins, or other appropriate carriers which may include pharmaceutically-advantageous adjuvants, such as preservatives, antibiotic or antimitotic agents, buffers, osmotic balancers, water, or electrolytes. A pharmaceutically- or physiologically-acceptable injectable carrier within the scope of the present invention will meet industry standards for sterility, isotonicity, stability, and non-pyrogenicity.

The solution is sterile-filtered under aseptic conditions by means of a membrane filter having a pore diameter of 0.22 micrometers and filled to 1 ml into 1 ml injection flasks (Brown) of Hydrolic Class 1. The injection flasks are sterilely closed with Teflon-coated rubber stoppers and provided with aluminum flanged lids. The 1 ml sterile injectable aliquot of solution contains 100 mg of active material.

The pharmaceutical composition may be in any form suitable for oral use, such as tablets, suspensions, dispersable powders, emulsions, capsules, or elixirs. Coloring, flavoring, sweetening, and preserving agents also may be provided.

Tablets containing the active ingredient or ingredients in a mixture with non-toxic pharmaceutically-acceptable excipients which are suitable for the manufacture of tablets are also within the scope of this invention. These excipients may be inert diluents, such as calcium carbonate, sodium carbonate, lactose, calcium phosphate; or binding agents, such as starch, gelatin, or acacia; or lubricating agents, such as magnesium stearate, stearic acid, or talc. Moreover, oral compositions may be coated by known techniques to delay disintegration and absorption in the gastrointestinal tract, thereby providing sustained action.

Aqueous suspensions, containing conventional suspending agents, dispersing agents, or wetting agents; preservatives, coloring agents, flavoring agents, and sweetening agents may be formulated in accordance with industry standards. Similarly, dispersable powders and granules for preparation of aqueous suspensions by the addition of water may be provided.

The optimal concentration of the hexacosanol is a function of a variety of factors, such as the desired frequency of application, mode of application, duration of effect, amount of repair and/or protection of neuronal tissue, severity of trauma or disease, results of toxicology studies, or the level of adverse side effects and considerations implicated by the chemical nature of n-hexacosanol or its carrier.

The exact dosage of the fatty alcohol for any particular application may be readily determined by standard animal and clinical testing techniques. However, the dosage unit compositions will contain a pharmaceutically-effective amount of the active ingredient.

For adult humans, this will generally be from about 0.5 mg to about 500 mg per dosage; more preferably, about 1 or 2 mg to about 100 or 200 mg per dosage. Greater amounts of the active compound may be used in controlled release compositions that release their active ingredient over a period of more than about 12 hours. Any of the conventional controlled-release vehicles may be used to advantage, including bioerodable materials, such as collagen, polylactic acid, and the like. Other controllable release materials include lattice-forming polymers, such as polymethylmethacrylate, gelatin, cellulosic materials, and the like.

Other pharmaceutical compositions falling within the scope of the present invention include combinations of the fatty alcohols described herein with other known neurotrophic or neuroprotective materials, utilizing the art-recognized effective concentrations or dosages of those materials. Such materials include nerve growth factor (NGF), fibroblast growth factor (FGF), somatomedins, benzodiazepines, kappa-receptor agonists, calcium channel blockers, and the like; and excitatory amino acid receptor antagonists, such as MK-801 (Merck, Sharp and Dome).

In a preferred embodiment of the invention, following the procedure in Example 1 (wherein part of the spinal cord is excised), after surgical exposure of the spinal cord via surgical technique, an area of the spinal cord or peripheral nerve is excised; and a neuronal implant that has been pre-exposed to hexacosanol (preferably taken from the fetal tissue of a donor of the same species as the recipient) is inserted at the excision site. Alternatively, the implant may comprise a polymer or protein impregnated with hexacosanol which releases the hexacosanol in a time-release fashion. These polymers or proteins may be used by themselves or in association with neural implants.

In order that the invention described herein may be more fully understood, the following examples are set forth. It should be noted that these examples are for illustrative purposes only and are not to be construed as limiting the scope of this invention in any manner.

EXAMPLE 1

Survival and Regeneration of Neurons Treated with Hexacosanol Prophylactically and Post-Trauma

Subjects

Male and female Sprague-Dawley rats of an initial weight of 200–220 g are behaviorally pre-tested prior to spinal cord injury, and those rats which are found to lie outside of the normal behavioral range are to be eliminated from the method.

Procedure

The animals are anesthetized and a subsequent laminectomy is performed at T-8. Traumatic injuries to the spinal cord are produced via the method disclosed by Wrathall, et al., *Exp. Neurology,* 88:108–122 (1985). The spinal column is exposed and stabilized and is positioned under a weight-drop device. The weight used is preferably about 6 to 7 g in weight, and is placed onto the dura of the spinal cord for 2 minutes in the control animals. After the injury is performed, the site of the trauma is surgically closed and post-operative anti-infection injections of antibiotics are performed. By changing the height from which the weight is dropped, the extent of final spinal cord trauma is altered, and numerous variations in height and weight are used in the experimental animals. The extent of the lesion is evaluated by histopathological and morphometric analysis. Various groups of animals with different degrees of injury exhibit mild, moderate, or severe functional deficit. In the experimental animals, the functional deficit is measured using the inclined plane test; an assignment of a motor score to each limb by combining various behavioral tests is made. The evaluations of the sensory and motor function allow for a qualitative analysis of the nature of the deficits and are useful to discriminate between the effects of different therapeutic agents. The ability of hexacosanol to affect early neurological recovery and improve post-traumatic blood flow is also determined.

The animals are injected daily intraperitoneally with hexacosanol, preferably at a concentration of 1 mg/kg, prior to the contusive injury of the spinal cord, with a second control group only injected with the pharmaceutically-acceptable excipient within which the hexacosanol is carried. The animals are then injured in the above-mentioned manner, such acute spinal cord injury resulting in a variety of histopathological changes, which may include the development of progressive ischemic necrosis and invasion of astrocytic processes and fibroblasts.

Four weeks after injury, the functional deficit is measured in each group, as previously described As the height of the weight drop increases, the animals show greater motor impairment. In the treated group, hexacosanol decreases the occurrence of motor impairment, as measured by the inclined plane test, relative to the control animals.

After performance of the overall behavioral and physiological analysis, the rats are anesthetized and the spinal cord tissue is processed to allow for a histopathological and morphometric analysis, wherein the extent of the lesion and the cavitation of the spinal cord at the lesion site in treated and untreated are compared. The results show that, in treated animals, the traumatized area and the amount of cavitation in that area are reduced, and the amount of axonal growth is increased. A variety of behavioral tests are performed on the animals to assess the relative functional deficit. These tests include toe spread, placing, withdrawal, righting, inclined plane, hot plate, and swim tests. In all of these tests, the treated animals perform better than the controls.

The method of the present invention may be used in conjunction with a neural tube or bridge which acts generally as an endoneurium. The neural tube or bridge acts as a substrate and guiding mechanism between cells to repair severed axons or processes. In addition to its guiding properties, such a neural tube may additionally provide a substrate onto which the axons may grow and connect; and block the detrimental proliferation of fibroblasts or astrocytes around and between the severed axons. The neural tube or bridge may be composed of biological or non-biological inert substances which provide an appropriate substrate for axonal or nerve process growth and reconnection. Additionally, the neural tube or bridge may be coated with a substrate such as laminin, fibronectin, or polylysine.

Complementary results are observed in the post-traumatic blood flow measurement. Spinal cord blood flow is determined in the dorsolateral funiculus in the middle of the injury site using the hydrogen clearance technique (E. D. Hall and D. L. Wolfe, J. Neurosuro., 64:951-961 (1986)). Measurements are taken at 10 minutes, 2 hours, and 4 hours following the contusion. Control animals exhibit a progressive fall in spinal cord blood flow in the hours following the injury. Some decrease is also observed in the hexacosanol-treated animals; however, the recorded blood flow at 2 hours and 4 hours is significantly greater in the hexacosanol-treated animals. This indicates that hexacosanol can retard or prevent the development of post-traumatic spinal chord ischemia.

EXAMPLE 2

Regeneration of Peripheral Nerves Treated with Hexacosanol Following Axotomy

Subjects

Sprague-Dawley rats were anesthetized with 35 mg/kg Nembutal. One sciatic nerve was exposed in the thigh and transected 2 mm distal to the ischial tuberosity. The nerve was again cut 8 to 14 mm caudally (four experimental groups), and the isolated nerve segment was removed. The nerve stumps were inserted into the ends of a silicone tube and secured to the tube with a single 9.0 epineural stitch at each tube end and separated by a gap varying from 8 to 14 mm. The animals were further divided in two groups: one receiving daily i.p. injections of hexacosanol (1 mg/kg) and the other receiving the pharmaceutically acceptable excipient only. Eight weeks after surgery, the animals were re-anesthetized and perfused with saline through the left ventricle of the heart. After approximately 450 ml were perfused, the sciatic nerve was removed and placed overnight in a fixative containing 3% paraformaldehyde and 0.1 M phosphate buffer (pH 7.4). The next day, the nerves were rinsed in the same buffer and placed into a solution of 1% osmium tetroxide for 2 hours. The tissue was then rinsed, dehydrated in ethanol and embedded in Spurr.

The nerves were examined as follows After hardening, thin sections were cut and placed on grids. Sections are made of the regenerated nerve midway between the proximal and distal stumps and 2 mm distal to each end of the tube. The number of myelinated axons were counted in 10 fields for each regenerated nerve using electron microscopy.

The percentage of successful regenerations were calculated for each group of rats and for each gap length. A successful regeneration was defined as a nerve cable containing at least 1,000 axons linking the proximal and distal stumps of the transected nerve. The number of successful regenerations decreased when the gap was increased from 8 to 14 mm in the control group; no successful regenerations were observed for gap values higher than 10 mm. In animals treated with 1 mg/kg hexacosanol i.p., the number of successful regenerations was higher compared to the control group and regeneration also occurs for gap values over 10 mm. Additionally, the number of regenerated axons decreased when the gap between the stumps increased. Also, the number of myelinated axons was higher in the hexacosanol treated animals as compared to the control animals.

EXAMPLE 3

Survival of Neurons Treated With Hexacosanol Following Axotomy

Subjects

Male Sprague Dawley rats (175-200 g) (n = 15), obtained from Charles River Labs (Wilmington, MA), were group-housed in a 12/12 hour light/dark vivarium. Rats were given free access to Purina Lab Chow ® and water. Body weights were recorded each day of the study.

Procedure

Two groups of rats were anesthetized with Nembutal (54 mg/kg); Abbott Laboratories, Chicago, IL) and placed in a stereotaxic instrument (David Knopf Instruments, Tujunga, CA) and given unilateral fimbria-fornix lesions by aspiration. Briefly, an incision was made in the scalp exposing the top of the skull and a 1 mm trench drilled from bregma along the lateral suture to expose the top of the brain. Suction was applied to a glass pipette to aspirate through the cortex, visualize, and ablate the fimbria-fornix. The fimbria-fornix and supracollosal striae was transected unilaterally (on the left side). After the ablation, when bleeding had stopped, Gelfoam ® (Upjohn, Kalamazoo, MI) was placed into the cavity over the exposed brain and the scalp was sutured. One group of rats (n = 11) were injected daily intra-peritoneally (i.p.) with hexacosanol (1 mg/kg Fluka) starting two days before surgery. Control rats (n = 4) were infused with a vehicle of 50% ethanol.

Two weeks after fimbria-fornix ablation, the rats were sacrificed and their brain extracted for AChE histochemistry. One hour before sacrifice, the rats were given an i.p. injection of 0.20 ml diisopropylfluorophosphate (DFP) in 2 ul/ml of sterile saline (Sigma Chemical Co.). The rats were given a lethal dose of Nembutal and perfused with phosphate buffered saline (PBS) followed by 4% formaldehyde in PBS, the brains extracted and post-fixed overnight in a solution containing 20% sucrose in 4% formaldehyde at 4° C. Coronal sections were cut at 25 um on a cryostat (Hacker Instruments, Fairfield, N.J.) and collected through the rostrocaudal extent of the septal nuclear area and through the lesion site, to ensure the lesion was complete. Boundaries for the regions of the septal nuclear area were as described by Gage et al. (Neuroscience 19:241-256 (1986)), incorporated by reference herein. Every fourth section was stained for Nissl bodies with cresyl violet, and every fifth section processed for visualization of AChE using tetraisopropylpyrophosphoramide. The percent of cholinergic neurons surviving after the lesion was determined from the AChE and cresyl violet-stained sections using a camera lucida attached to an Olympus light microscope.

The numbers of large and small neurons (large neurons indicate that cells were healthy and surviving) in the septum and diagonal band staining positive for AChE were counted by two independent rats who were not aware of the experimental conditions. The percent of surviving cholinergic neurons in the septum and diagonal band for the damaged and intact sides of the brain was analyzed using analysis of variance. To determine if there were significant differences between the groups, an analysis of variants and a Scheffe F-test was used for post-hoc analyses.

Figure 2A:
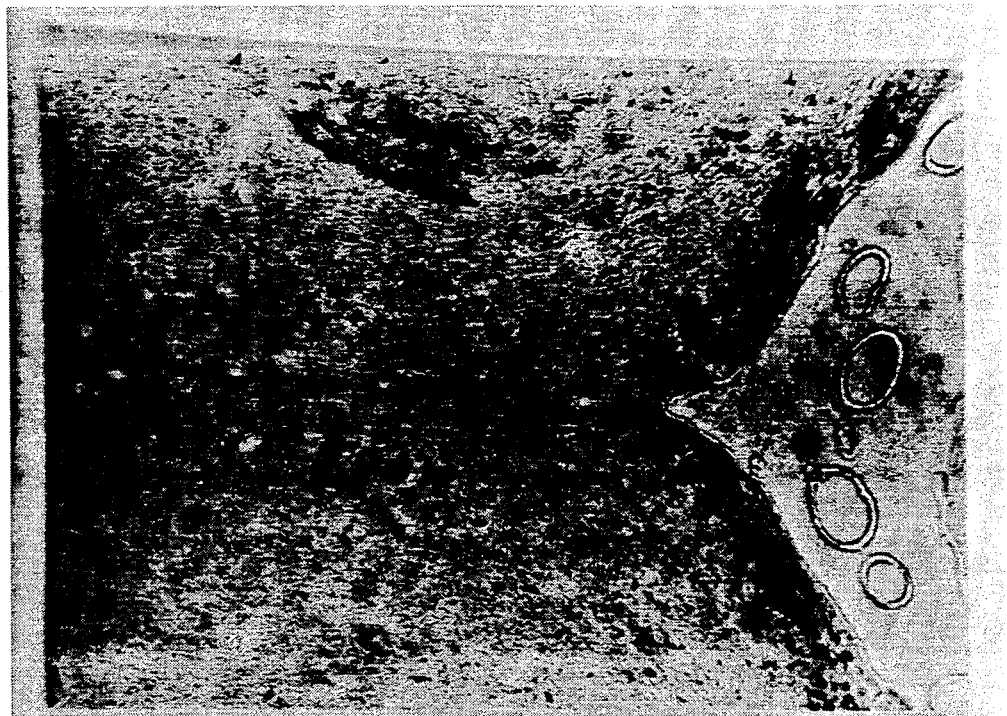
FIGS. 2A and 2B provide, photomicrographs of AChE-stained neurons in the septal area of rat brain; a: animals with a unilateral transection of the fimbria-fornix on the left side of the brain; A: a control animal; B: an animal with a fimbria-fornix lesion that received hexacosanol (arrows indicate the midline of the section; #1 indicates the medial septum and #2 indicates the vertical diagonal band area in the damaged side of the brain) as described in Example 3, infra.
Figure 2B:
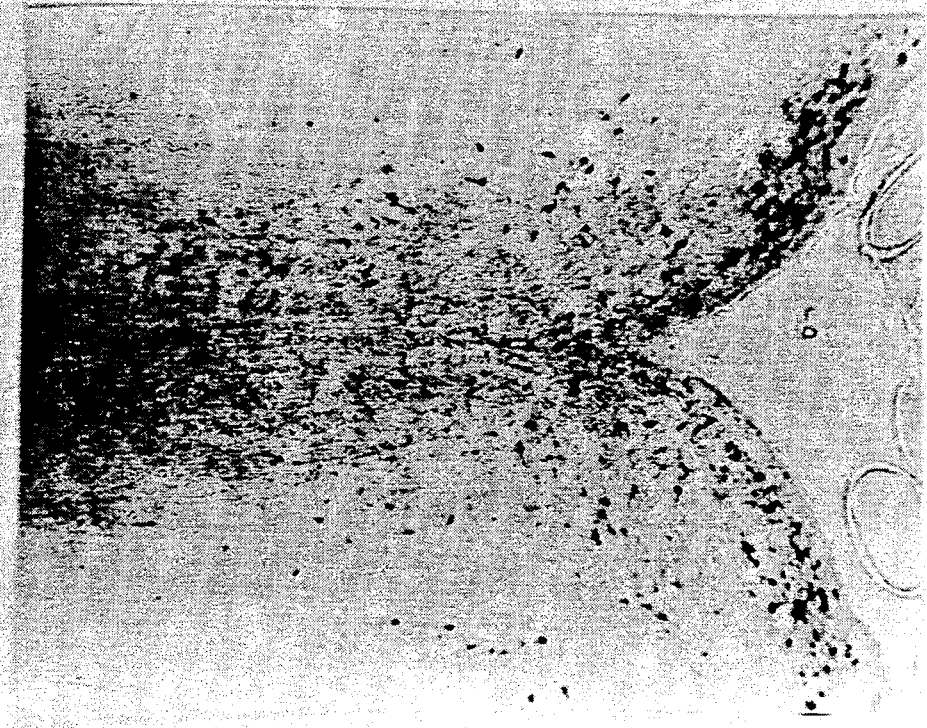
Figure 4A:
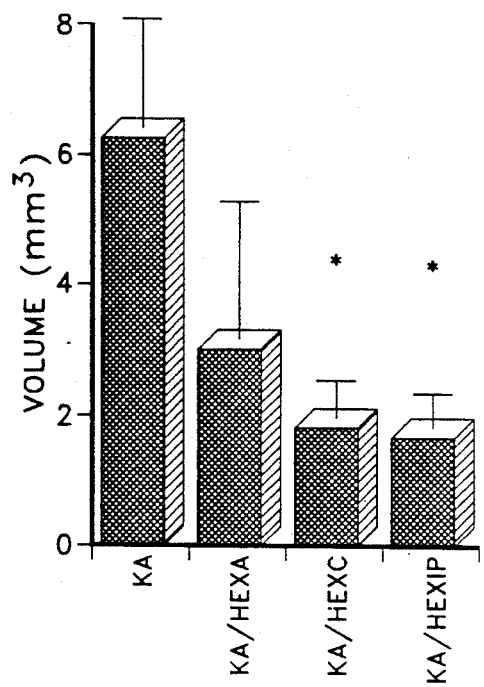
FIGS. 4A–4B are a graphic depiction of the volume of cell loss in the hippocampal region of the brain in three (3) groups of animals treated with kainate (KA), and kainate plus hexacosanol (HEX), as described in Example 4, infra.
Figure 4B:
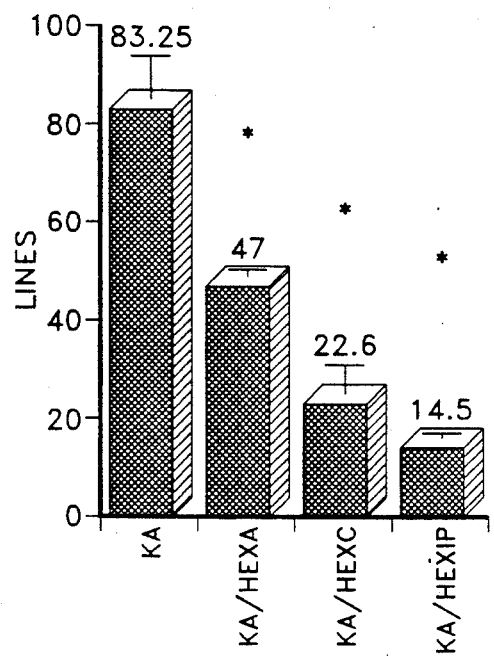
Figure 4C:
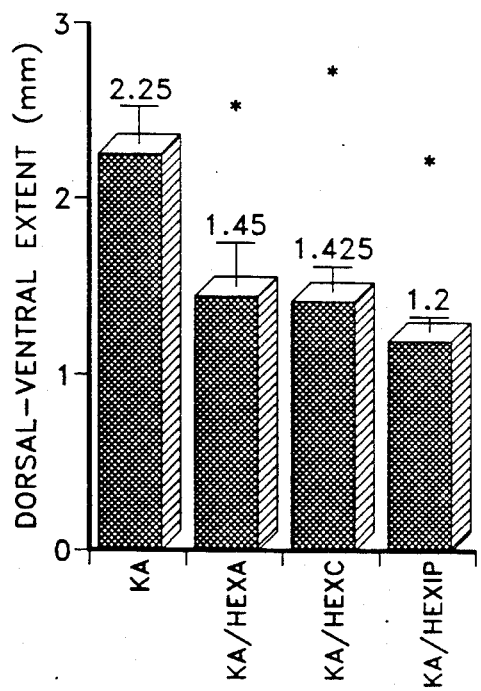
Figure 4D:
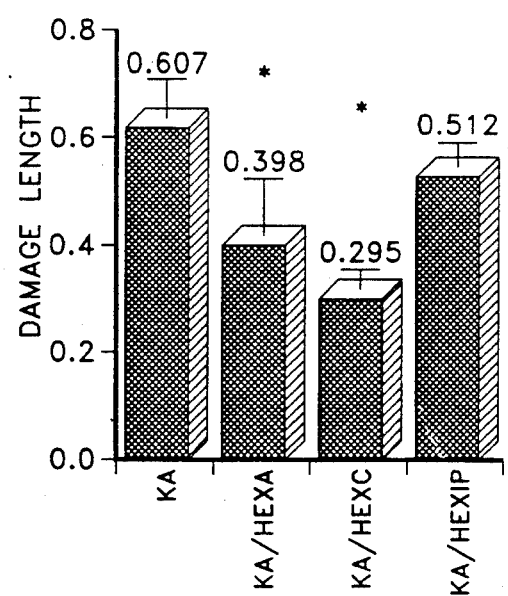

Examination of the photomicrographs of AChE-stained neurons provided in FIG. 2 reveals a loss of AChE-positive neurons after fimbria-fornix transection in untreated animals, relative to hexacosanol-treated animals, where neuronal death was reduced.

Figure 3:
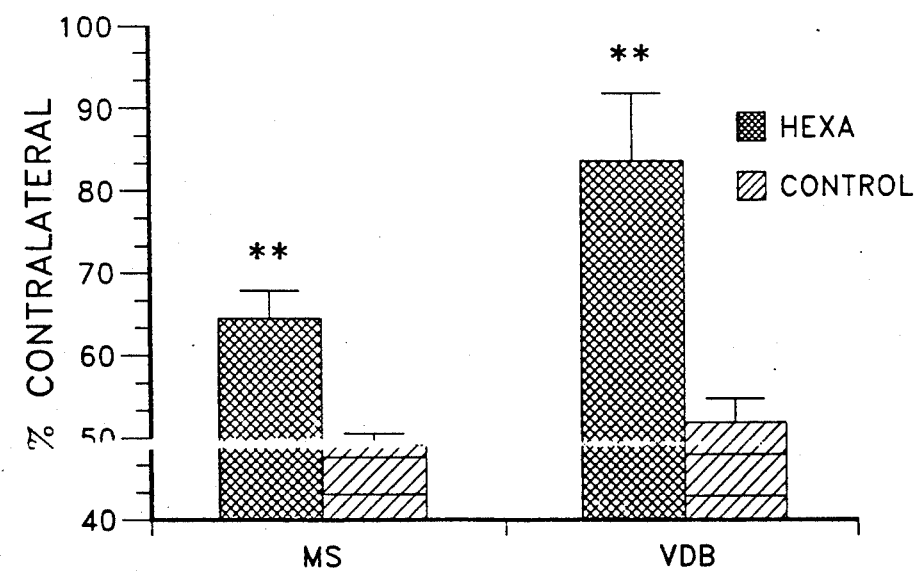
FIG. 3 is a graphic depiction of the percent survival of cholinergic neurons in lesioned and intact medial septum (MS) and the vertical limb of the diagonal band (VDB) in the forebrains of hexacosanol-treated and untreated (control) animals, as described in Example 3, infra.

As shown in FIG. 3, the number of large cholinergic neurons present two weeks after axotomy on the side of the lesion was significantly greater ($P < 0.05$) in the treated, compared to the untreated, group of animals.

These data demonstrate that the long-chain fatty alcohol hexacosanol administered peripherally (i.p.) in vivo will prevent the loss of cholinergic neurons in the medial septum (MS) and vertical diagonal band (VDB).

Maintaining neuron survival after injury may have little effect on functional outcome if the neurons are not permitted their proper afferent and efferent connections. In many cases, damage to the CNS is incomplete (i.e., there is not a complete severing of a pathway). When damage to a pathway is partial, surviving neurons can use the pathway to send projections to the denervated areas. This, in turn, may also increase the viability of the remaining neurons. In the case of a total separation of the pathway (e.g., from lesion), the neurons with axotomized projections undergo retrograde degeneration that results in cell death, such as in the fimbria-fornix lesion paradigm that results in loss of septal cholinergic neurons. Promoting neuronal survival with applications of neurotrophic factors, or using the methods of the invention to administer long-chain fatty alcohols such as hexacosanol, may require additional interventions since nerve cell loss may occur when the neurons do not reconnect with their hippocampal targets; or the supply of neurotrophic factors is no longer available.

Thus, the present invention also encompasses methods of promoting continued survival of neurons after injury by administering long-chain fatty alcohols, such as hexacosanol, and providing a "neural bridge" from materials that allow surviving neurons to send projections to connect to their appropriate target cells.

Various neural bridges have been described but have not been shown to promote or improve cell survival (Aguayo, "Axonal Regeneration from Injured Neurons in the Adult Mammalian Central Nervous System," In Synaptic Plasticity, C. W. Cotman (Ed.), New York, Gilford Press, pp. 457–484 (1985); and Aguayo, et al., *Annals of the New York Academy of Sciences*, 495:1–9, (1987)). Such neural bridges could provide a substrate for neurons to send out axonal projections that span areas that normally exceed the capacity of the regenerating neurons to overcome. Such bridges may also permit the axon to avoid areas of dense gliosis (accumulation of glial cells in damaged areas of the CNS) that can normally impede reinnervation. A dramatic example of these bridges is the use of peripheral nerve segments successfully joining the medulla oblongata and upper thoracic spinal cord of an injured rat, over an area of 35 mm (David and Aguayo, *Science*, 214:931–933 (1981)). Connectivity between the septum and hippocampus has also been demonstrated using implants of peripheral homogenates of neurons (Wendt, *Brain Res. Bull.*, 15:13–18 (1985)). Thus, if neuron survival can be promoted through application of long-chain fatty alcohols such as hexacosanol, as described herein, it may be possible to establish proper connectivity by providing a neural bridge. The neural bridge may consist of biological materials such as homogenates of neurons, or placenta, or even whole neurons. Alternatively, the bridge could be constructed of a synthetic, biologically-compatible material; for example, a polymer such as polylysine or laminin. Once the proper reconnectivity is established, the survival of the previously denervated neural structures will be supported by the biochemical interactions through the reestablished nerve network.

EXAMPLE 4

Prevention of Excitotoxin-Induced Neuron Death

Subjects

Male Sprague Dawley rates (n = 33) (175–200 g), obtained from Charles River Labs (Wilmington, MA) were group-housed in a 12/12 hour light/dark vivarium. Rats were given free access to Purina Lab Chow ® and water. Body weights were recorded each day of the study.

Procedure

Rats received intra-hippocampal injections of 3.75 moles KA (6 ul; KA from Sigma Chemical Co., St. Louis, MO). The animals were divided into four groups: (1) control animals given intra-cerebral injections of either saline or 50% ethanol approximately 5 minutes before the KA (n = 6); (2) animals given 2.5 moles hexacosanol in 1 ul ethanol (Fluka), injected intra-cerebrally approximately 5 minutes before the KA ("KA/HEXA"; n=9); 3) animals given daily intra-peritoneal injections of hexacosanol (1 mg/kg) starting 2 days before surgery and during 7 days after KA injection ("KA/HEXIP"; n=6); and 4) animals receiving both daily intra-peritoneal injections and intra-cerebral injection of at the time of KA injections, as in Groups 2 and 3 ("KA/HEXC"; n=12).

For the surgical procedures, animals were anesthetized with Nembutal (54 mg/kg; Abbott Laboratories, Chicago, Ill.) and were placed into a stereotaxic instrument (David Kopf Instruments, Tujunga, Calif.). An incision was made in the scalp exposing the top of the skull and a hole drilled to expose the top of the brain. The rats received unilateral injections of KA and hexacosanol via a Hamilton syringe (Hamilton Co., Reno, Nev.). After retracting the syringe, Gelfoam ® (Upjohn, Kalamazoo, Mich.) was placed over the exposed brain and the scalp was sutured. Rats in the control groups received similar surgical treatment, but received saline rather than KA injections On the seventh day after KA injections, the rats were sacrificed and their brains extracted for histological analysis.

The rats were given a lethal dose of Nembutal and perfused with phosphate-buffered saline (PBS), followed by 4% formaldehyde in PBS; the brains extracted and post-fixed overnight in a solution containing 20% sucrose in 4% formaldehyde at 4° C. Horizontal sections were cut at 25 um on a cryostat (Hacker Instruments, Fairfield, N.J.) and collected throughout the entire brain. Every sixth section was stained for Nissl bodies with cresyl violet. The total volume of the hippocampal CA fields was measured on both sides (KA-injected and non-injected controls) in all sections, to determine the amount of damage, particularly in hippocampal fields CA3-CA4. The extent of the damage was measured with the cresyl violet-stained sections using a camera lucida attached to an Olympus light microscope. Quantification was done by projecting the tissue section images onto a digitizing pad interfaced with a computer having the appropriate software programs for determining the length of the structures.

As show in FIG. 4, the size (volume) of lesions in the hippocampus caused by intra-cerebral injections of the excitotoxin KA was reduced. All three groups treated with hexacosanol demonstrated a protective effect against the excitotoxin injury.

These results demonstrate that the long-chain fatty alcohol hexacosanol administered to the region of excitotoxin injury reduces the extent of neural death from excitotoxin lesions.

EXAMPLE 5

Acceleration of Recovery of Behavioral Function of Injured Neurons After Treatment With Hexacosanol

Subjects

Thirty-five male Sprague Dawley rats (175-200 g), obtained from Charles River Labs (Wilmington, MA), were housed two-per-cage in a 12/12 hour light/dark vivarium. Rats were given free access to Purina Lab Chow®. During maze acclimation, pre-training and post-surgery testing, the rats were placed on a water deprivation schedule. Water was used as the reward for correct performance during the testing procedure. Animals were allowed to drink for 10 minutes each day at least 40 minutes after completing the behavioral testing. The rats weighed 150-175 g at the beginning of the study. Body weight was recorded each day of testing. Testing was done during the light phase of the vivarium cycle.

Surgery

Two days before the entorhinal lesion mini-osmotic pumps (Alza Model 2002, Alzet, Palo Alto, CA) were implanted to provide chronic infusion of either hexacosanol (5 umole in 50% ethanol) (Sigma Chemical Co., St. Louis, Mo.) or the carrier solution alone (50% ethanol). Rats were anesthetized with Nembutal (54 mg/kg; Abbott Laboratories, Chicago, IL) and placed into a stereotaxic instrument (David Kopf Instruments, Tujunga, Calif.). The head was elevated 50, an incision made in the scalp exposing the top of the skull, and a hole drilled to expose the top of the brain. A 25-gauge stainless steel cannula was lowered into the lateral ventricle (from bregma: A/P±0.0, M/L,−1.5, D/V−3.5) and position secured by dental acrylic anchored by a stainless steel screw set into the skull. The mini-osmotic pumps were secured to the cannula and inserted subdurally between the shoulder blades and the scalp was sutured. Tubing (0.020×0.060 mm) connected the cannula with the mini-pump The mini-pumps were weighed, filled with either hexacosanol or carrier solution, and weighed again to determine the amount of solution in each pump.

For the entorhinal lesions, rats were anesthetized with Nembutal (54 mg/kg) and placed into a stereotaxic instrument (David Kopf Instruments, Tujunga, Calif.). An incision was made in the scalp exposing the top of the skull and a hole drilled to expose the entorhinal cortex. The head was elevated 10 and the stereotaxic arm set at a 10° angle away from the midline There were a total of 9 lesion sites, with coordinates from lambda at A/P±0.0, M/L±3.3, D/V −−2.0, 4.0, 6.0; A/P±0.0, M/L±4.1, D/V±−2.0, 4.0, 6.0; A/P±1.0, M/L±5.1, D/V±−2.0, 4.0, and 6.0. At each site, a #2 stainless steel insect pin, insulated except at the tip, was lowered and an electrolytic lesion was made in the entorhinal region by passing 1 mA current for 45 seconds. After retracting the electrode, Gelfoam ® (Upjohn, Kalamazoo, Mich.) was placed over the exposed brain and the scalp was sutured. Rats in the control groups received similar surgical treatment, but the electrode was not lowered into the brain.

Reinforced-Alternation Task

Each rat was handled for four days prior to T-maze acclimation. On the last day of handling, the rats were placed on water deprivation (i.e., access limited to 10 min. per day). The T-maze was constructed of wood with each arm being 600 cm high. Maze acclimation was conducted for three days as follows: On Day 1, each rat was placed into the "Start" section of the T-maze and was allowed to move freely in the maze for 3 minutes. At each end-of-the-goal arms, a plastic dish containing 1.5 ml of water was located, which was replaced after the rat exited the goal arm. Day 2 was similar to Day 1, but after entering the goal arm, the rat was allowed to drink; removed from the goal arm; the water replaced; and the rat placed in the start arm. Day 3 was similar to Day 2, but the gates to the goal arms were closed after the rat entered the reward area. All testing was done at the same time each day.

The reinforced-alternation task was initiated by placing the rat in the start section of the T-maze, facing the back wall. The animal was then allowed to traverse the maze and enter one of the goal arms. On the first trial of each day, the animal was rewarded for entering either arm of the maze. After a correct choice, the rat received 1.5 ml of water and was allowed 10 seconds to drink. Thereafter, reward was given only if the rat entered the arm opposite the one previously rewarded. The rats were tested on 10 alternation trials per day. If a rat failed to make an alternation choice after 1 minute, the trial was considered an error. Pre-training lasted for 5 consecutive days. At the end of pre-training, all rats were performing at 90% correct alternations on the spatial task. After pre-training, rats were assigned to experimental groups equated for performance in the alternation task. There were three experimental conditions: (1) rats without lesions receiving saline (n=12); (2) rats with unilateral entorhinal lesion receiving saline (n=12); and (3) rats with unilateral entorhinal lesions receiving hexacosanol (n=11). There were no differences between groups during pre-training. Testing on the reinforced-alternation task was started 3 days after surgery and lasted for 15 consecutive days.

Figure 5:
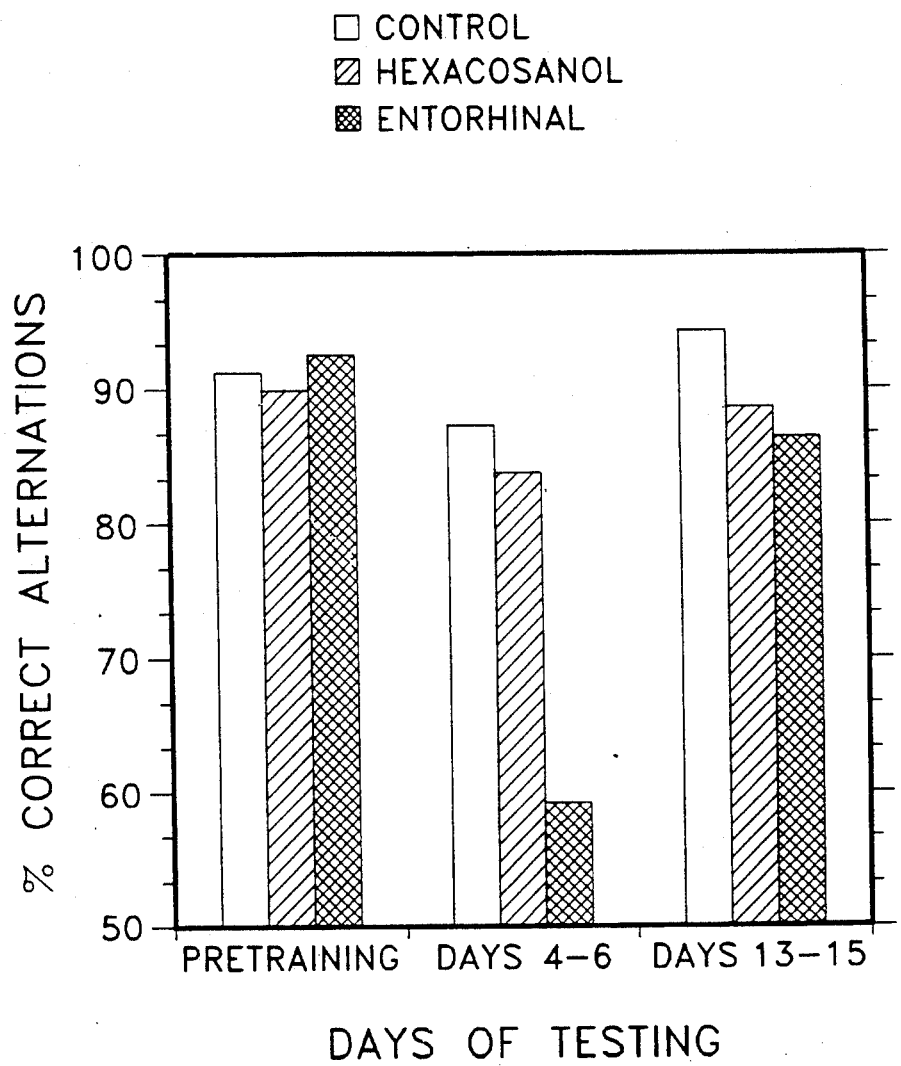
FIG. 5 is a graphic depiction of the percent correct alternations made by animals with lesions of the entorhinal cortex, both treated with hexacosanol and untreated, and by animals without lesions (control), as described in Example 5, infra.

The results of the spatial alternation task were analyzed using analysis of variance and post-hoc comparisons using a Scheffe F Test. There were significant differences between groups (F=10.96, p>0.001) and across the days of testing (F=31.48, p>0.001). Rats with lesions of the entorhinal cortex made significantly fewer correct alternations than the rats without lesions for the first 10 days, showing a gradual improvement across testing. Treatment with hexacosanol after entorhinal lesion reduced the behavioral deficit such that these rats did not suffer significantly from the rats without lesions. FIG. 5 illustrates these results. On Days 4–6 after surgery, animals with lesions of the entorhinal cortex exhibited a significant decrease in performance ability not present in the lesioned group of animals treated with hexacosanol. All groups of animals performed about 90% correct alternations by 12–15 days of testing post-surgery.

Histological Analysis

After the last day of behavioral testing, the rats were sacrificed for verification of lesion placement and size. The brains were extracted, placed in dry ice, and 25 um horizontal sections cut on a cryostat (Hacker Instruments, Fairfield, NJ). Every seventh section was stained with cresyl violet and every eighth section for the presence of acetylcholinesterase (AChE) using tetraisopropylpyrophosphoramide for sections taken through the entire brain.

Examination of the sections (using an Olympus microscope) indicated the lesions eliminated the majority of the entorhinal cortex and angular bundle. Loss of the hippocampal afferents from the angular bundle resulted in a dense increase of AChE-positive fibers in the outer molecular layer of the dentate. The apparent expansion of the cholinergic fibers into the outer molecular layer verified the loss of nerve input to the entorhinal region. As shown in FIG. 5, even with such neural damage, animals treated with the hexacosanol demonstrated a faster behavioral recovery than lesioned animals untreated with hexacosanol.

These results indicate that treatment with hexacosanol can promote recovery from learning and memory impairment after damage to the brain. The restoration of cognitive capacity is of critical importance for treating neural loss due to trauma or disease. While the cognitive deficits in the present example recover after extensive experience, it could also be expected that some improvement may occur on tasks that do not show as complete a recovery. Behavioral recovery is a balance between degeneration and recovery mechanisms that serve relevant behaviors. It is likely that hexacosanol has multiple actions, enhancing function of existing pathways as well as acting on degenerative processes. Whatever the mechanisms, it is clear that hexacosanol can act on neural function to facilitate recovery of behavior in injured neurons in vivo. This has important therapeutic implications for treatment of trauma, stroke, and neurodegenerative diseases.

In addition to accelerating behavioral recovery after neural injury, hexacosanol may improve the absolute extent of recovery achievable after injury. For example, a subject having sustained neural injury may be able to reach a higher level of behavioral function or performance after treatment with hexacosanol than would be possible in the absence of hexacosanol administration. The extent of recovery may vary with the difficulty of the task confronting the individual.

In addition, administration of hexacosanol may reduce the rate of impairment of behavioral function over time as neural injury while a disease progresses.

The present invention thus provides methods for the use of hexacosanol and certain analogues (e.g., long-chain fatty alcohols containing from 23 to 29 carbons, or prodrug esters thereof) to promote the survival of injured neurons in the CNS, and possible the PNS.

Although the invention has been described with reference to particular examples, it should be understood that various modifications can be made to provide still other modifications and embodiments which promote the survival of neurons (e.g., using compositions containing certain analogues of hexacosanol, or using compositions containing hexacosanol in combination with other compounds for treating injured neurons), without departing from the spirit of the invention. Therefore, it will be appreciated that the scope of the invention is to be defined by the following claims.

What is claimed is:

1. A method for treating injury to or disease of neurons in a mammal, comprising the step of administering to neurons of said mammal in vivo a therapeutically effective amount of a composition comprising one or more long-chain fatty alcohols having from about 23 to about 29 carbon atoms, or a prodrug ester thereof.

2. The method of claim 1 wherein said injury to neurons comprises traumatic injury.

3. The method of claim 2, wherein said injury to neurons results from surgery.

4. The method of claim 1 wherein said injury to neurons is due to stroke.

5. The method of claim 1 wherein said injury to neurons comprises chemical injury.

6. The method of claim 5, wherein said chemical injury is caused by excitotoxic agents.

7. The method of claim 1, wherein said disease results from a neurodegenerative condition.

8. The method of claim 7, wherein said administration is effective to slow the destruction of neurons resulting from the progress of said neurodegenerative condition as compared to the progress of destruction of neurons in an untreated mammal that has said neurodegenerative condition.

9. The method of claim 1, wherein said administration is effective to promote recovery of neuronal function after said injury.

10. The method of claim 1, wherein said administration improves recovery of learning and memory functions in a mammal that has of learning and memory functions in an untreated mammal that has sustained a loss in neuronal function.

11. The method of claim 10, wherein said loss of function is caused by a disease selected from the group consisting of Alzheimer's disease, Huntington's Chorea, Epilepsy, Parkinson's disease, Cerebral Palsy and Down's Syndrome.

12. The method of claim 1, wherein said administration is effective to reduce the rate of impairment that occurs over time as neural injury or disease progresses.

13. The method of claim 1, wherein said composition protects said neurons from damage or death due to exposure to neurotoxic agents.

14. The method of claim 1, wherein said neurons are central nervous system neurons.

15. The method of claim 1, wherein said neurons are peripheral nervous system neurons.

16. The method of claim 1, wherein said administration is effective to promote survival of said injured neurons.

17. The method of claim 1, wherein said administering step is performed after said injury.

18. The method of claim 1, wherein said long-chain fatty alcohols are in the form of a substantially purified extract of a plant in which said alcohols are naturally present, said extract obtained from said plant using an organic solvent.

19. The method of claim 1, wherein said composition is administered topically, orally, sublingually, bucally, vaginally, or parenterally.

20. The method of claim 1, wherein administration is by means of intra-cerebral, intra-peritoneal, intramuscular, intra-ventricular, or intra-venous injection.

21. The method of claim 1, further comprising the co-administration of an effective amount of at least two different long chain fatty alcohols having from about 23 to about 29 carbons, or a prodrug ester thereof.

22. A method for protecting neurons from injury or disease in a mammal, comprising the step of administering to neurons of said mammal in vivo a therapeutically effective amount of a composition comprising one or more long-chain fatty alcohols having from about 23 to about 29 carbon atoms, or a prodrug ester thereof, said composition administered prior to said neurons sustaining an expected injury or administered to subjects suspected of propensity for a disease affecting said neurons.

23. The method of claim 22, wherein said composition protects neurons against loss of function due to exposure to excitotoxic agents.

24. The method of any one of claims 1, 2–6, 9, 10, 13, 23, 14, 15, or 16, wherein said alcohol is n-hexacosanol.

* * * * *